(12) United States Patent
Nam et al.

(10) Patent No.: US 10,940,198 B2
(45) Date of Patent: Mar. 9, 2021

(54) HERPES ZOSTER VACCINE COMPOSITION

(71) Applicants: MOGAM INSTITUTE FOR BIOMEDICAL RESEARCH, Yongin-si (KR); INFECTIOUS DISEASE RESEARCH INSTITUTE, Seattle, WA (US)

(72) Inventors: Hyo Jung Nam, Yongin-si (KR); Eun Mi Kim, Yongin-si (KR); Duck Hyang Shin, Yongin-si (KR); Steven G. Reed, Bellevue, WA (US); Kang Il Yoo, Yongin-si (KR); Sung Jun Hong, Seoul (KR)

(73) Assignees: MOGAM INSTITUTE FOR BIOMEDICAL RESEARCH, Yongin-si (KR); INFECTIOUS DISEASE RESEARCH INSTITUTE, Seattle, WA (US)

( * ) Notice: Subject to any disclaimer, the term of this patent is extended or adjusted under 35 U.S.C. 154(b) by 0 days.

(21) Appl. No.: 16/473,393

(22) PCT Filed: Dec. 20, 2017

(86) PCT No.: PCT/KR2017/015155
§ 371 (c)(1),
(2) Date: Jun. 25, 2019

(87) PCT Pub. No.: WO2018/124615
PCT Pub. Date: Jul. 5, 2018

(65) Prior Publication Data
US 2019/0328868 A1    Oct. 31, 2019

(30) Foreign Application Priority Data
Dec. 26, 2016 (KR) .................. 10-2016-0178793
Dec. 20, 2017 (KR) .................. 10-2017-0176122

(51) Int. Cl.
*A61K 39/25* (2006.01)
*A61P 31/22* (2006.01)
*A61K 31/7024* (2006.01)
*A61K 31/01* (2006.01)
*A61K 39/00* (2006.01)
*A61K 39/39* (2006.01)
*G01N 33/569* (2006.01)

(52) U.S. Cl.
CPC .............. *A61K 39/25* (2013.01); *A61K 31/01* (2013.01); *A61K 31/7024* (2013.01); *A61K 39/39* (2013.01); *A61P 31/22* (2018.01); *G01N 33/569* (2013.01); *A61K 2039/55572* (2013.01)

(58) Field of Classification Search
None
See application file for complete search history.

(56) References Cited

U.S. PATENT DOCUMENTS

2011/0104260 A1    5/2011  Hanon et al.

FOREIGN PATENT DOCUMENTS

| JP | 2012528892 A | 11/2012 | |
|---|---|---|---|
| KR | 10-2004-0030599 A | 4/2004 | |
| KR | 10-2007-0110413 A | 11/2007 | |
| KR | 10-2009-0079209 A | 7/2009 | |
| KR | 10-2010-0063030 A | 6/2010 | |
| KR | 10-2014-0022799 A | 2/2014 | |
| WO | 2010141861 A1 | 12/2010 | |
| WO | 2012/141984 A1 | 10/2012 | |
| WO | WO2017/210364 | * 12/2017 | ............... A61K 9/12 |

OTHER PUBLICATIONS

Dendouga et al., "Cell-mediated immune responses to a varicella-zoster virus glycoprotein E vaccine using both a TLR agonist and QS21 in mice" Vaccine vol. 30 pp. 3126-3135 (Year: 2012).*
Anderson et al., "Physicochemical characterization and biological activity of synthetic TLR4 agonist formulations" Biointerfaces vol. 75 pp. 123-132 (Year: 2010).*
Rhea N. Coler, et al., "Development and Characterization of Synthetic Glucopyranosyl Lipid Adjuvant System as a Vaccine Adjuvant", PLoS ONE, e16333, 2011, pp. 1-12, vol. 6, issue 1.
International Search Report for PCT/KR2017/015155 dated Apr. 26, 2018 [PCT/ISA/210].
Korea Intellectual Property Office, Communication issued in Korean Patent Application No. 10-2017-0176122 dated Mar. 8, 2019.
Stacie L. Lambert et al., "Molecular and Cellular Response Profiles Induced by the TLR4 Agonist-Based Adjuvant Glucopyranosyl Lipid A", Plos One, Dec. 2012, vol. 7, No. 12, p. e51618 (11 pages total).

* cited by examiner

*Primary Examiner* — Eric Olson
(74) *Attorney, Agent, or Firm* — Sughrue Mion, PLLC

(57) ABSTRACT

The present invention relates to a herpes zoster vaccine composition, which comprises glycoprotein E of Varicella zoster virus, a glucopyranosyl lipid adjuvant, and a metabolic oil, and selectively increases a cell-mediated immune reaction without having disadvantages of attenuated live vaccines, thereby exhibit high safety and a high preventive effect against herpes zoster.

8 Claims, 18 Drawing Sheets

Specification includes a Sequence Listing.

[Fig. 1]
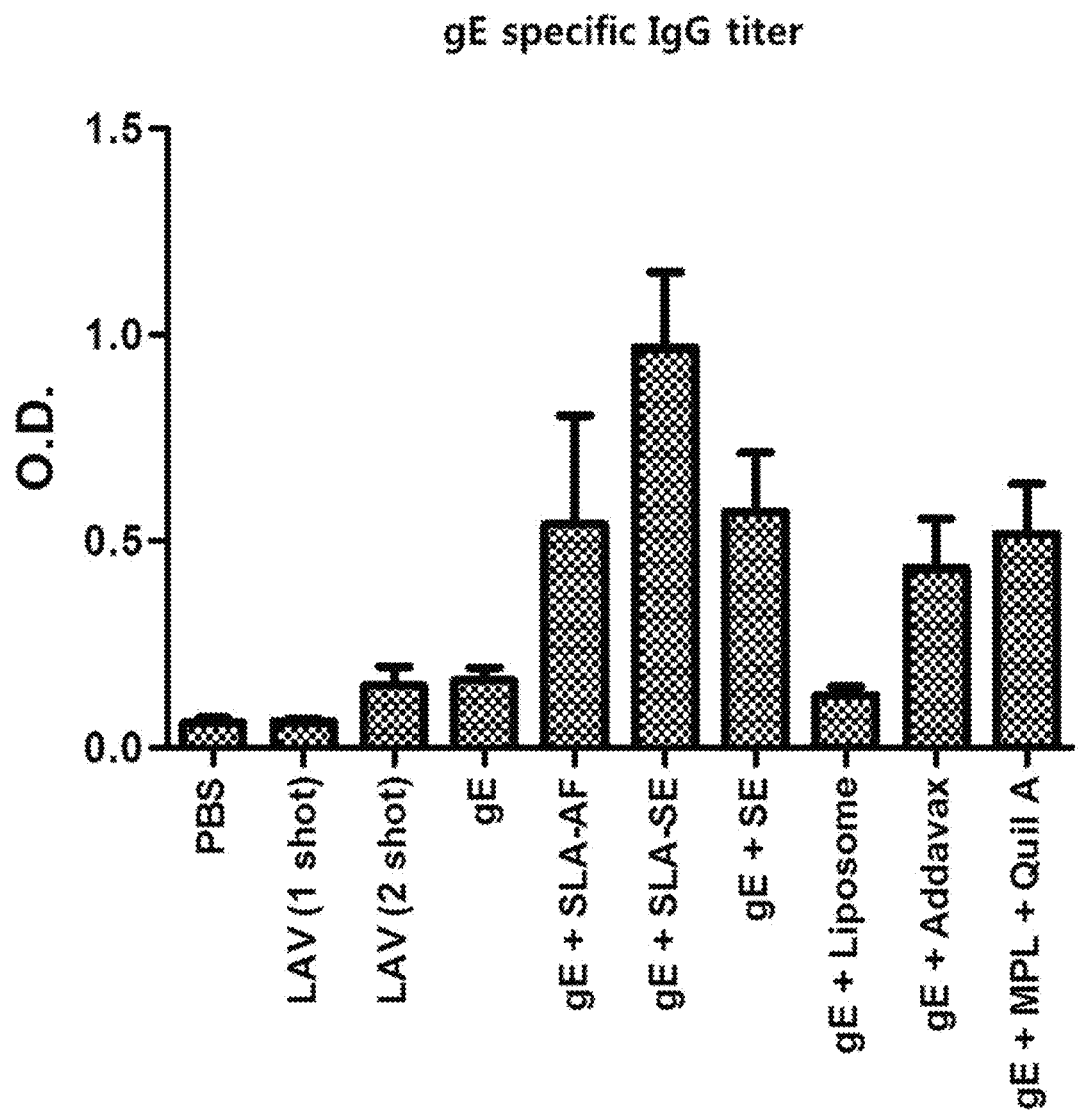

[Fig. 2]
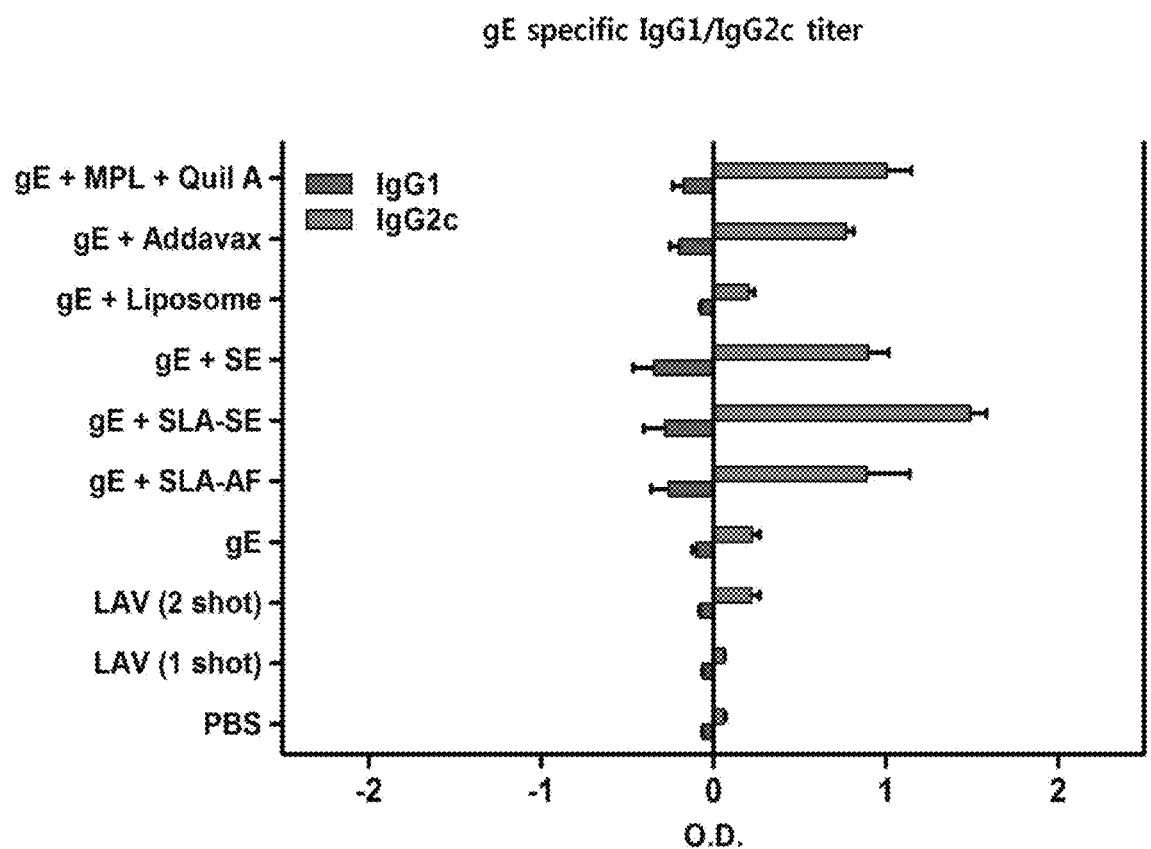

[Fig. 3]
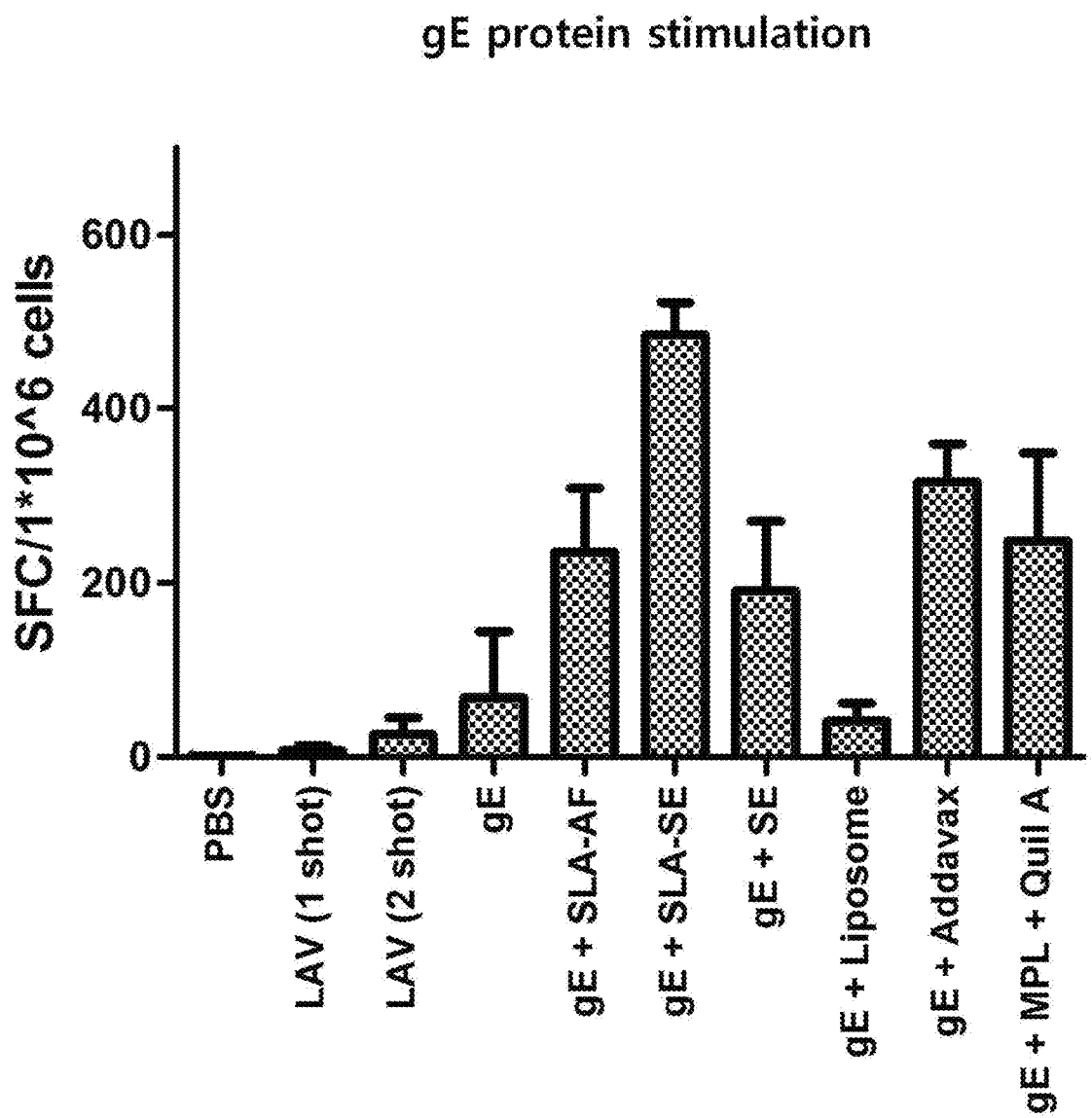

[Fig. 4]
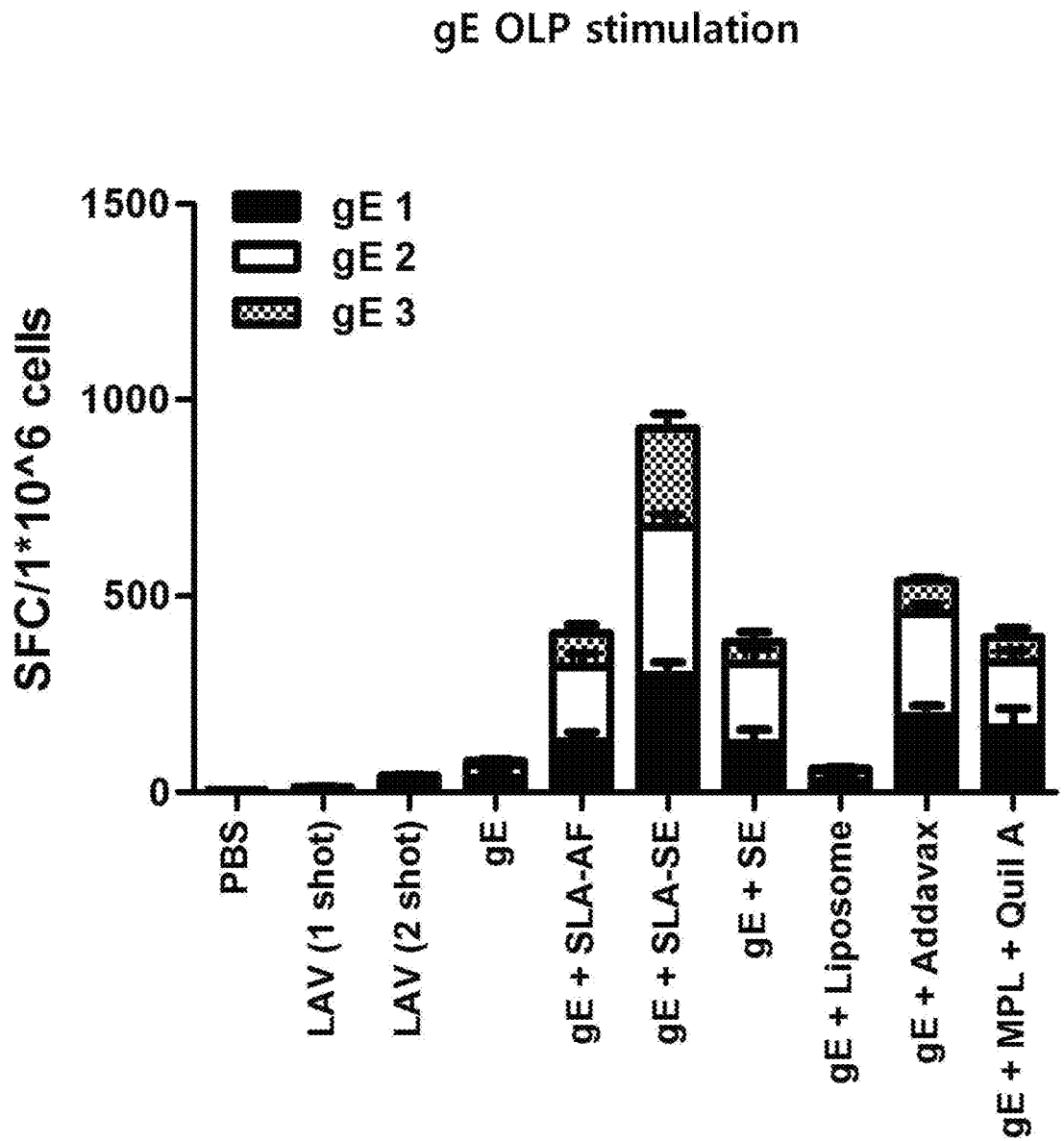

[Fig. 5]
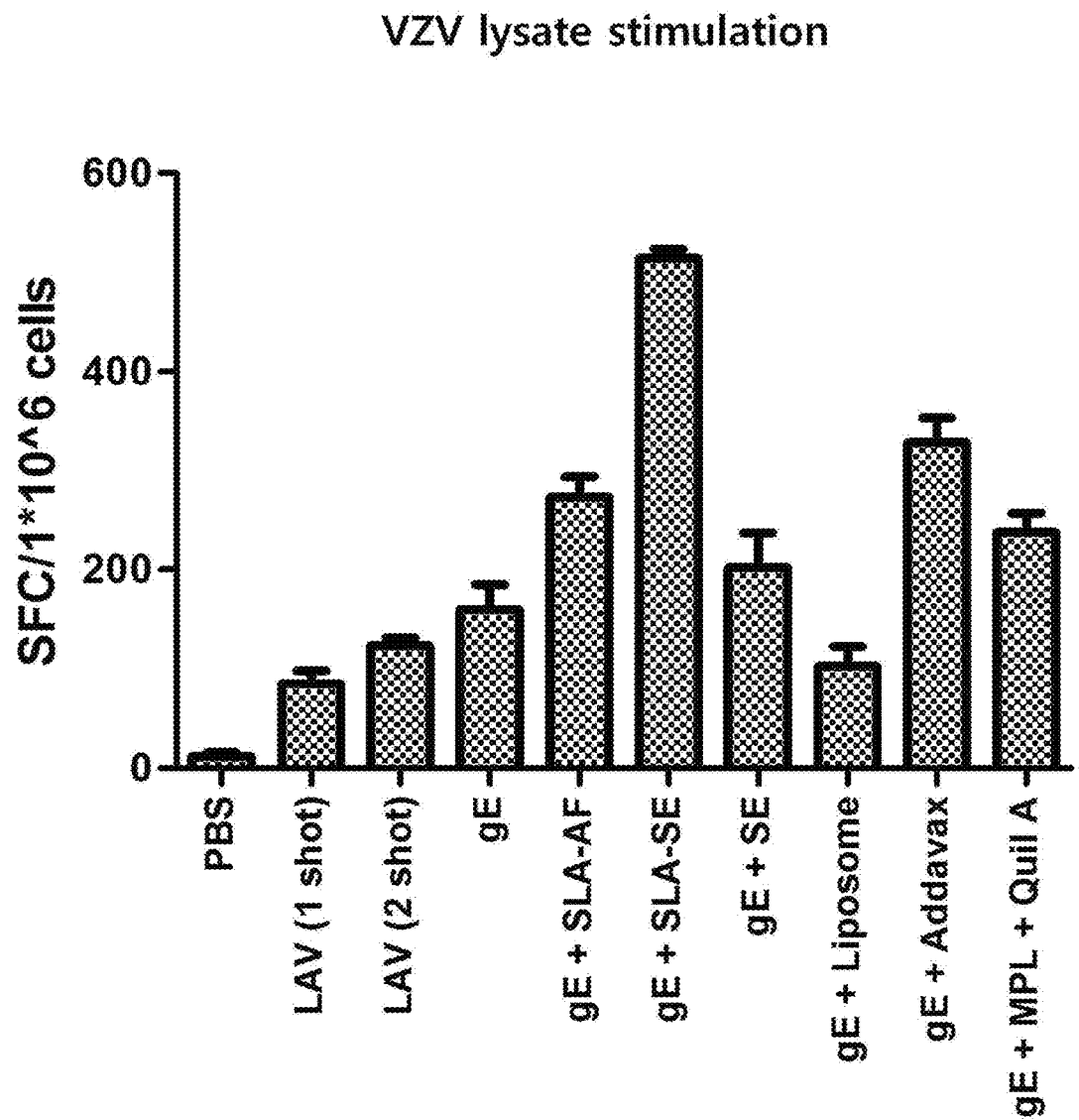

[Fig. 6]
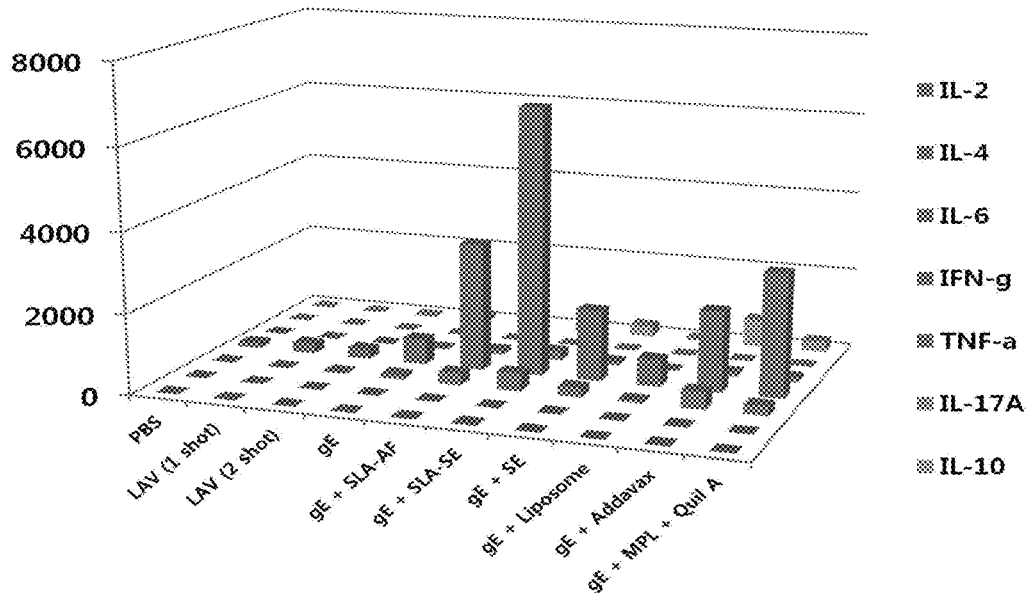
[Fig. 7]
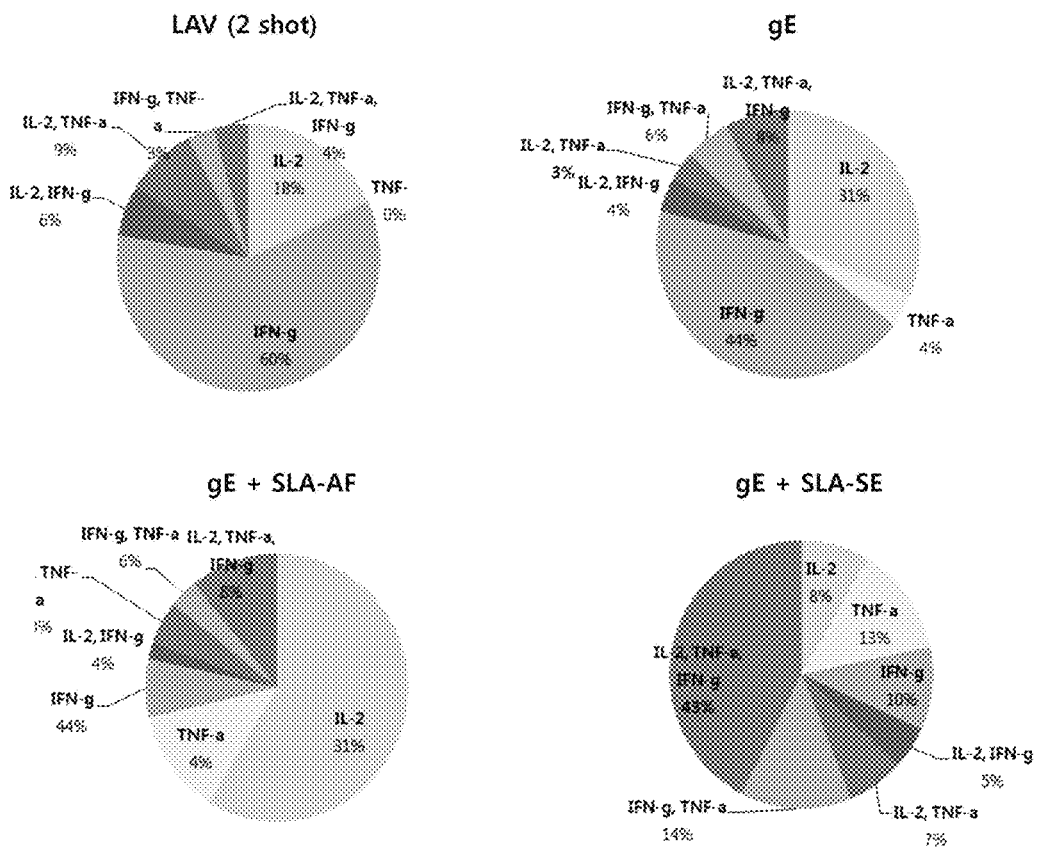

[Fig. 8]
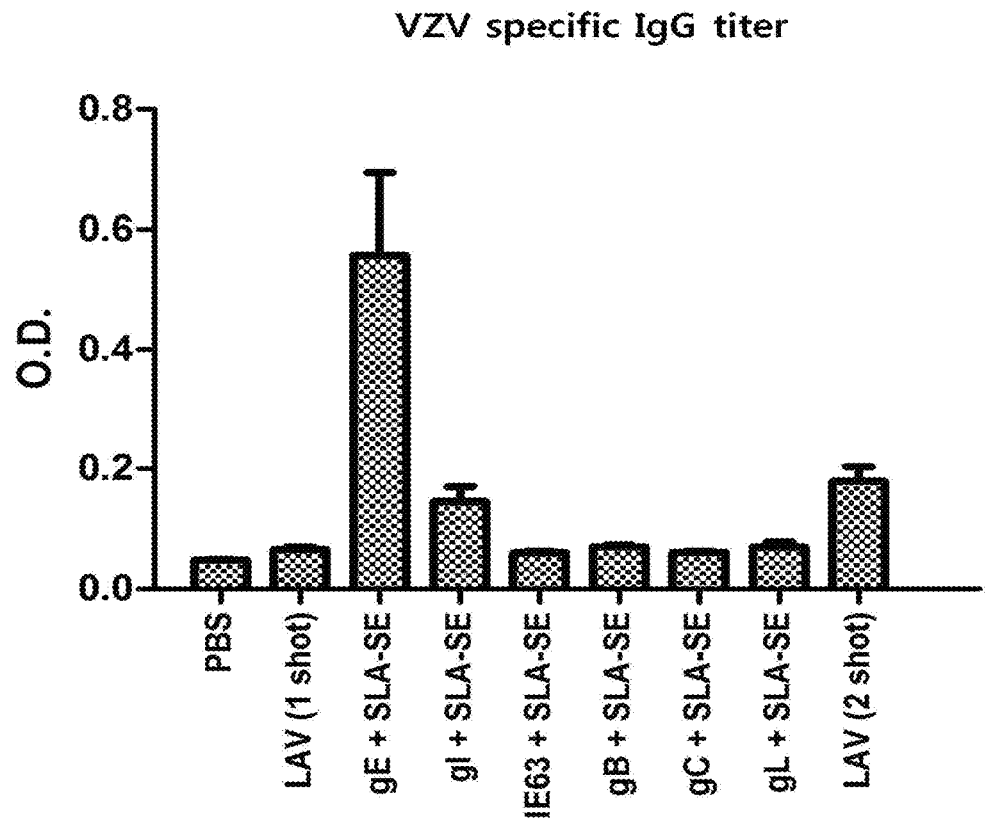
[Fig. 9]
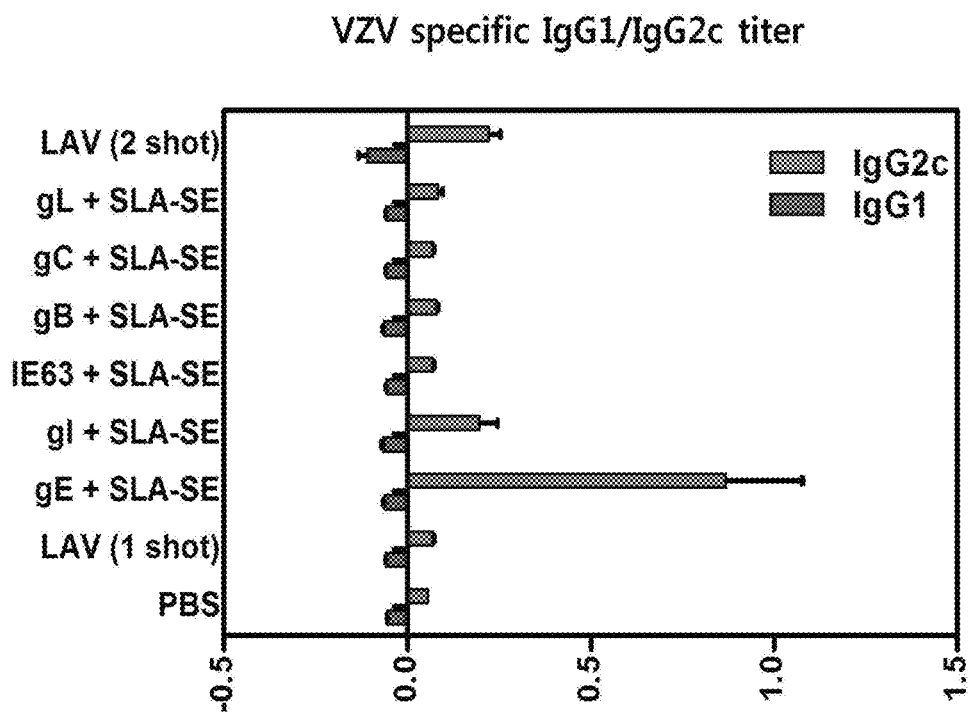

[Fig. 10]
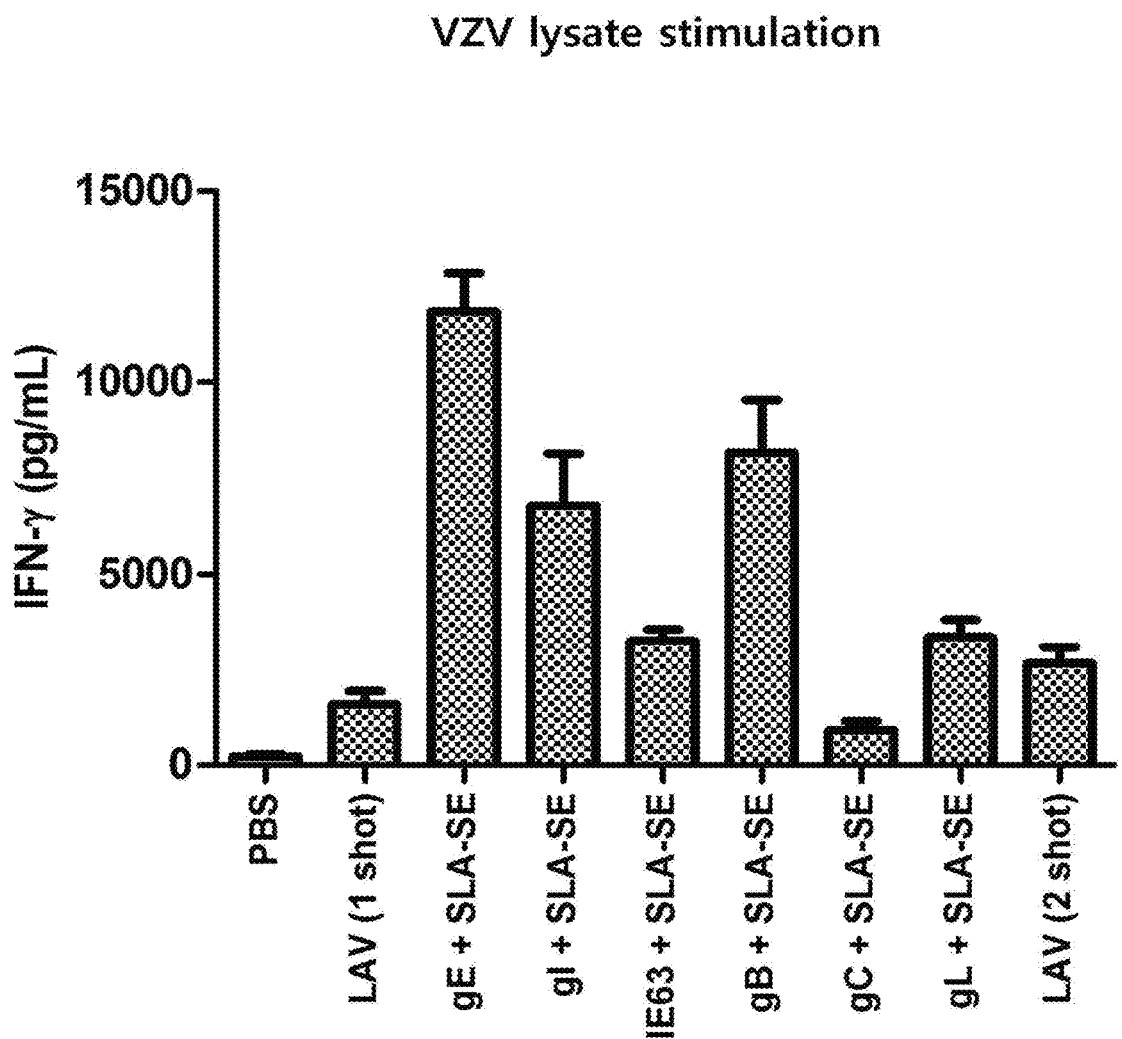

[Fig. 11]
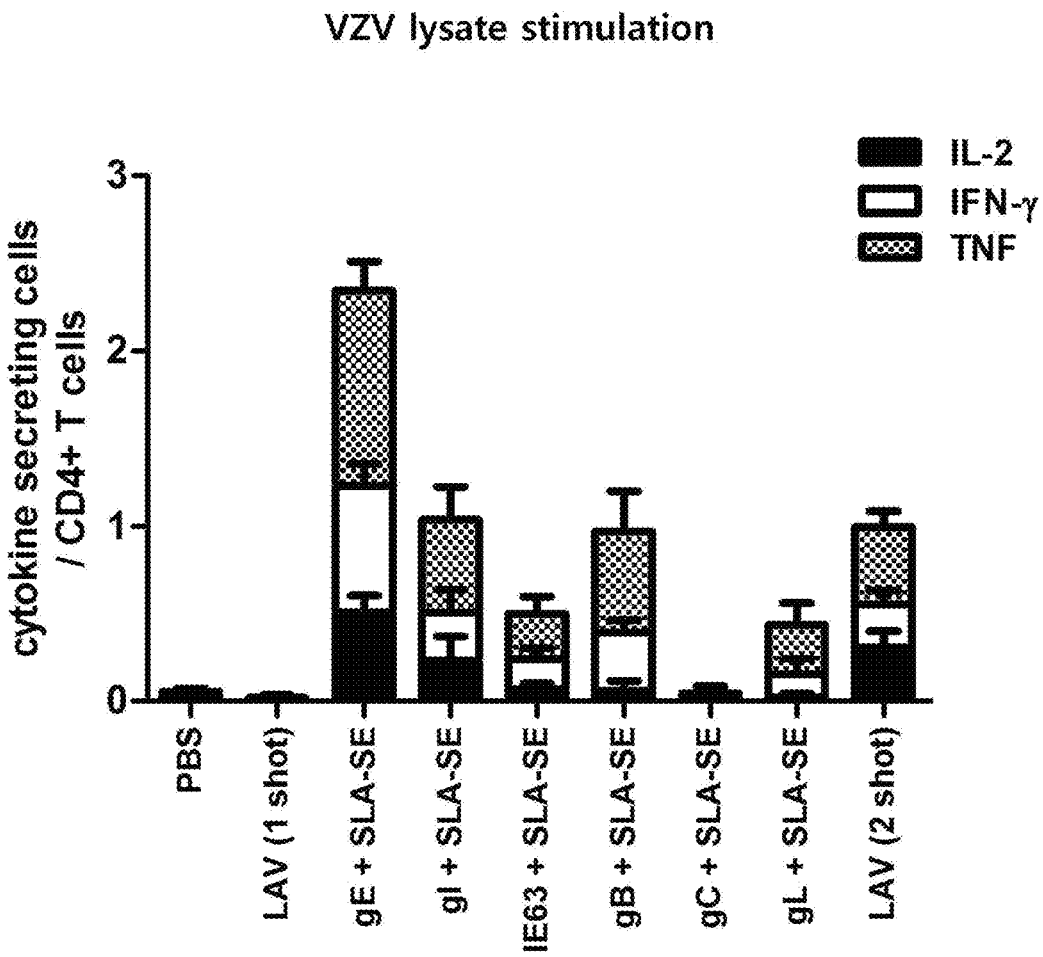
[Fig. 12]
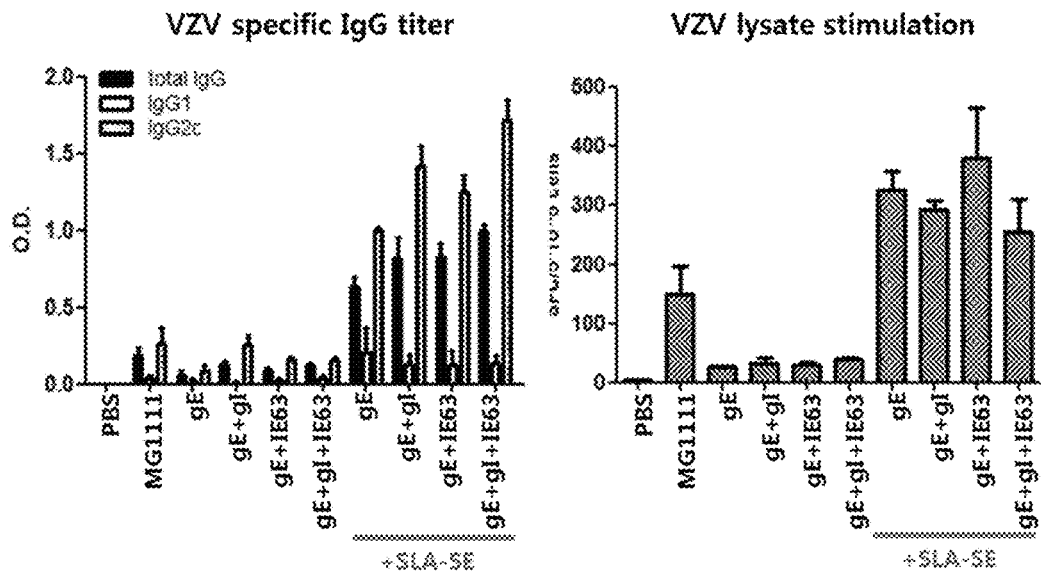

[Fig. 13]
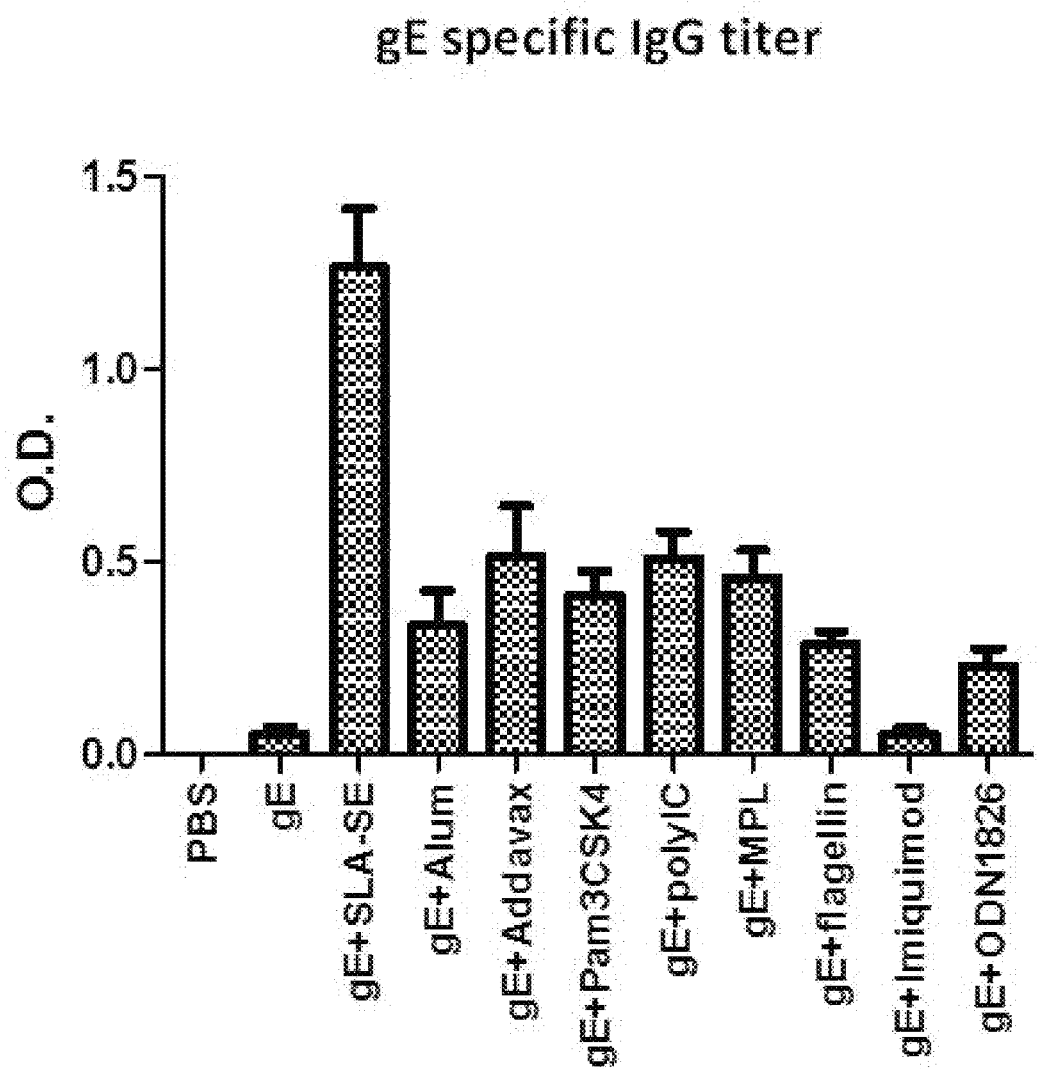

[Fig. 14]
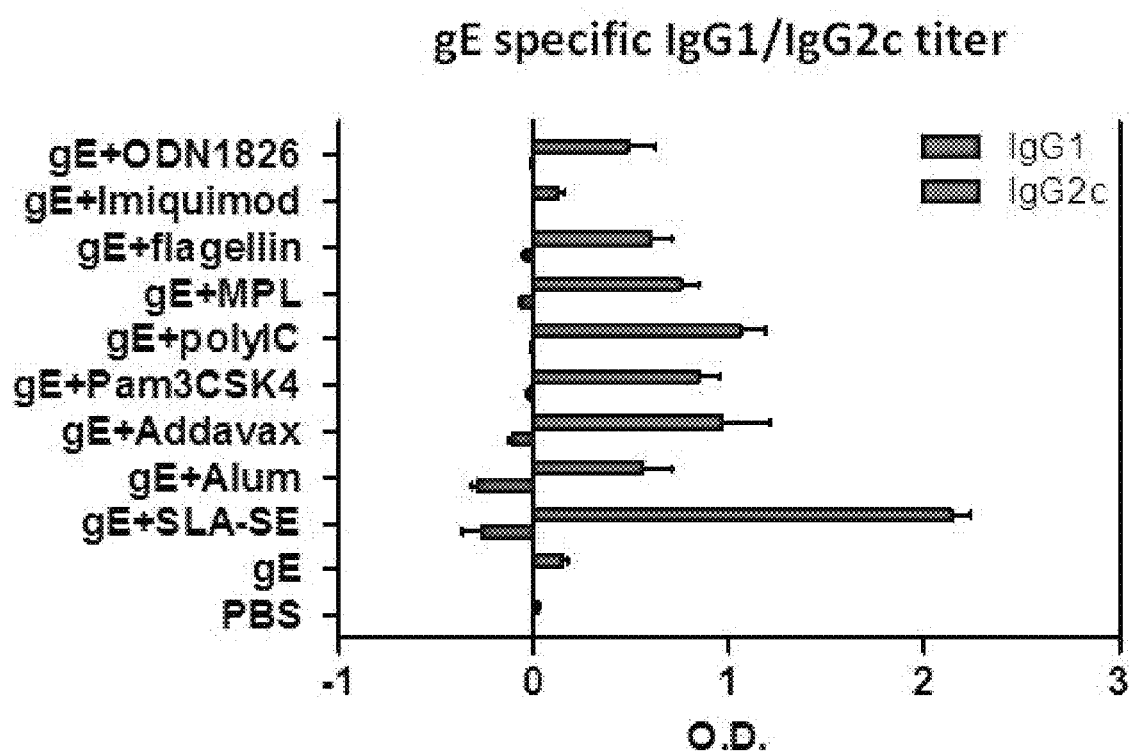

[Fig. 15]
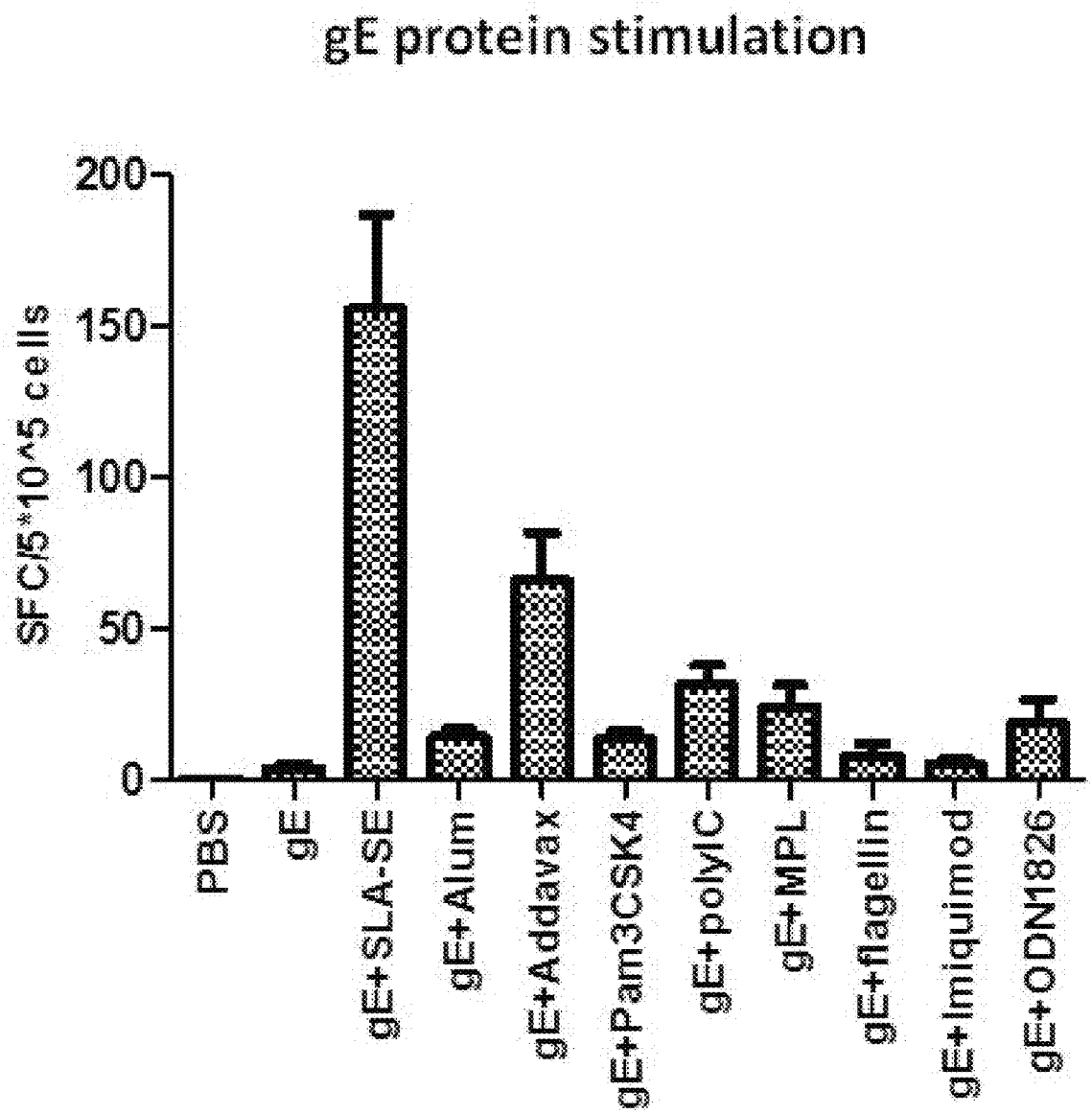

[Fig. 16]
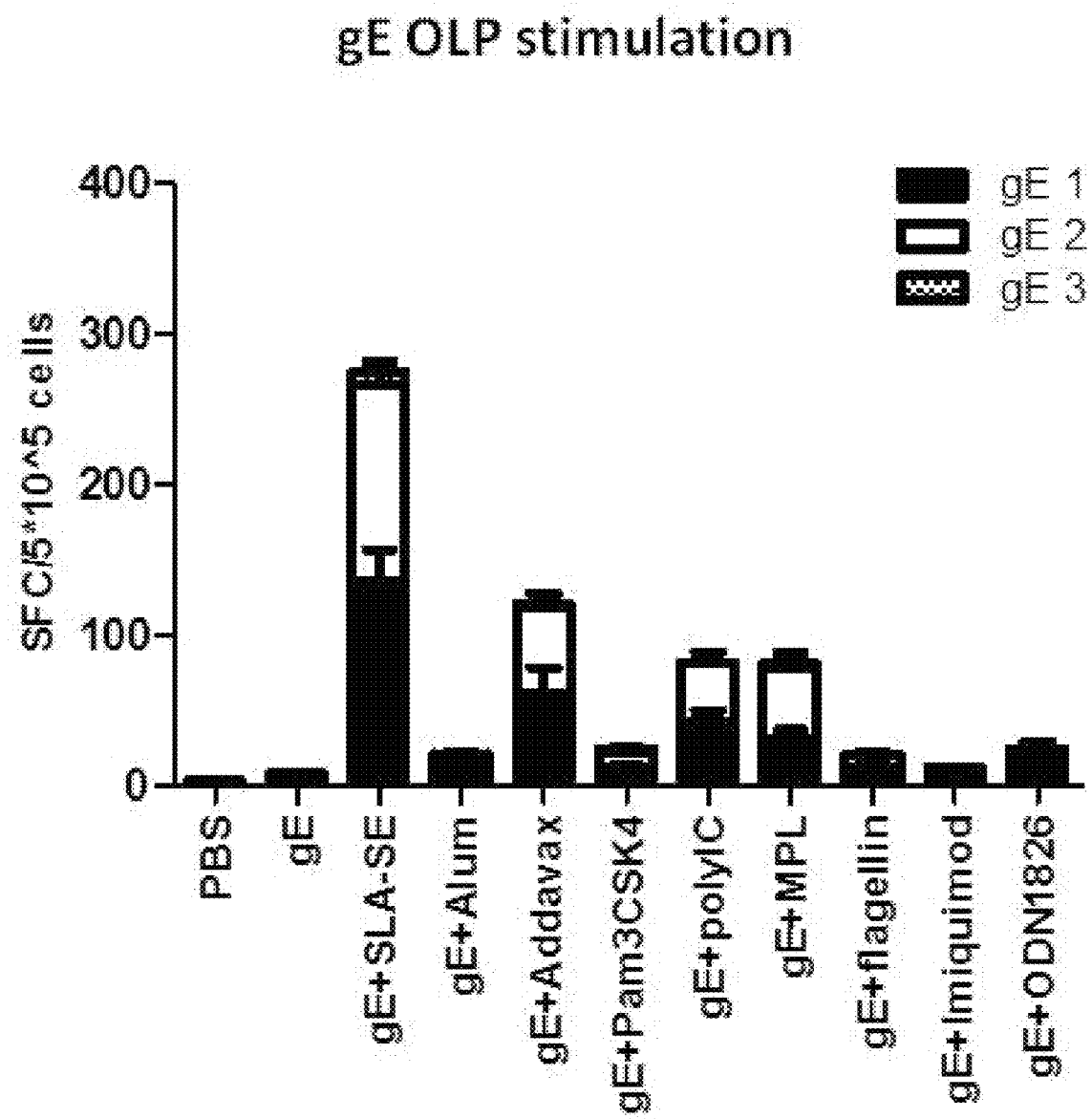

[Fig. 17]
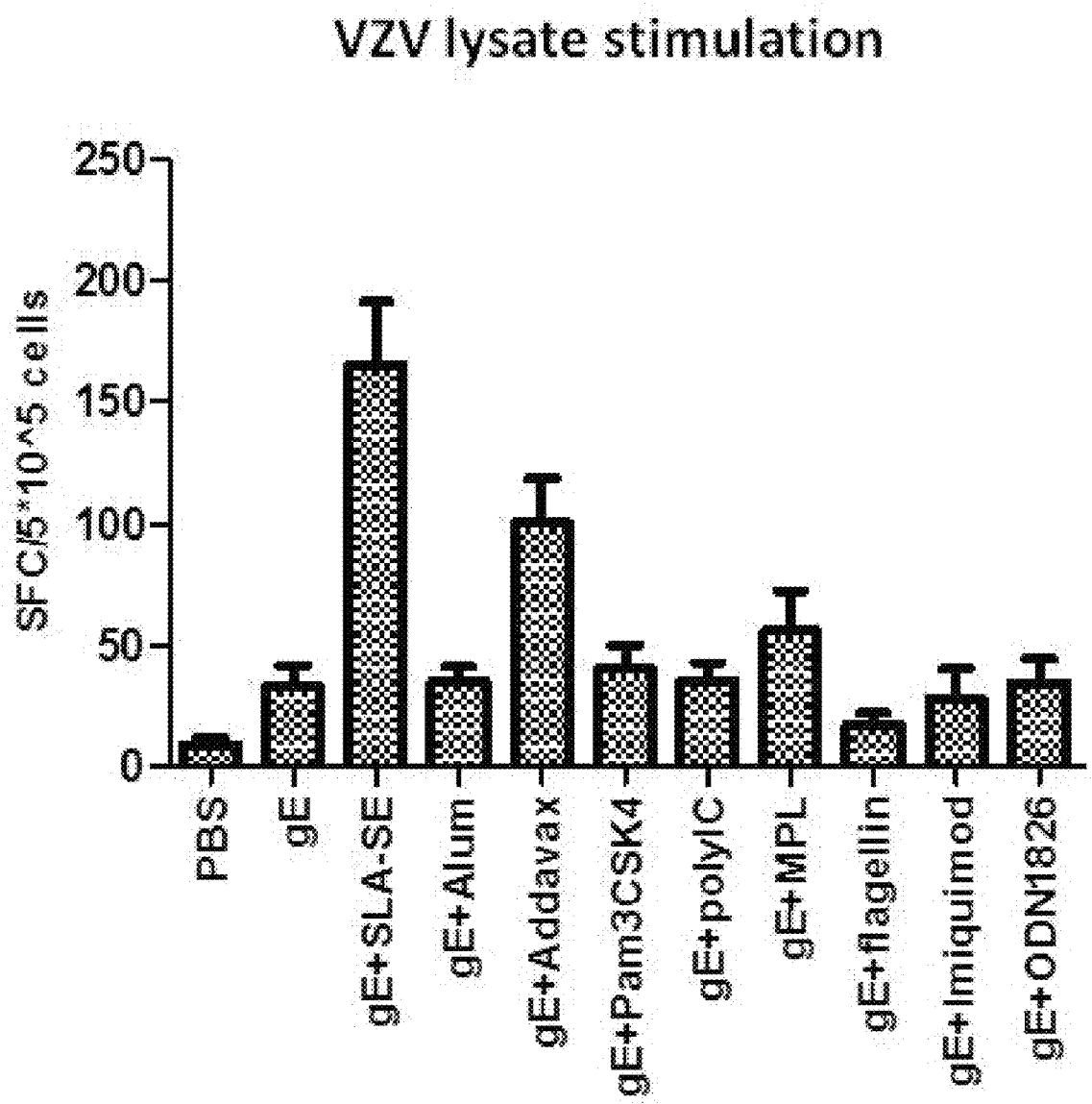

[Fig. 18]
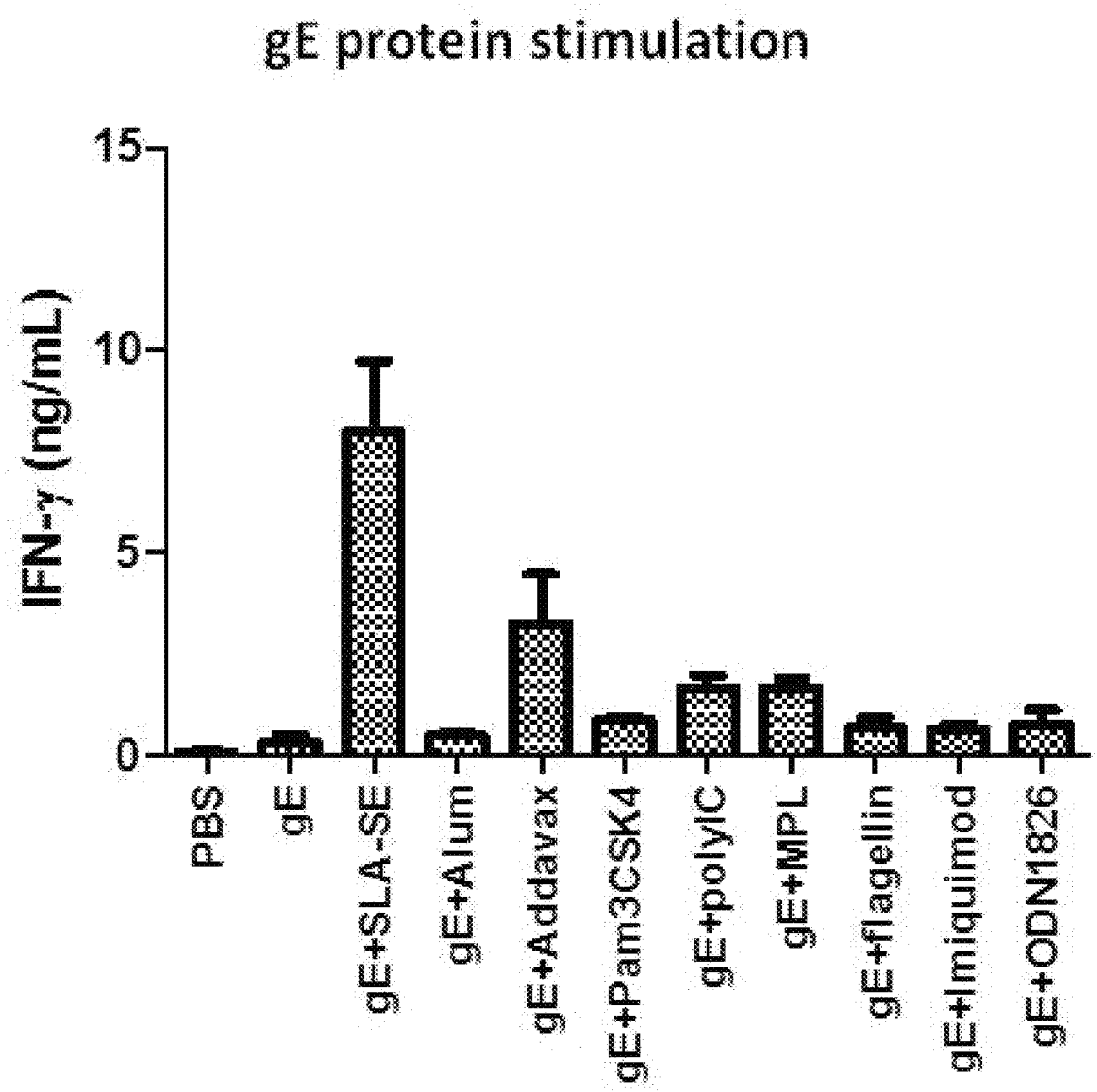

[Fig. 19]
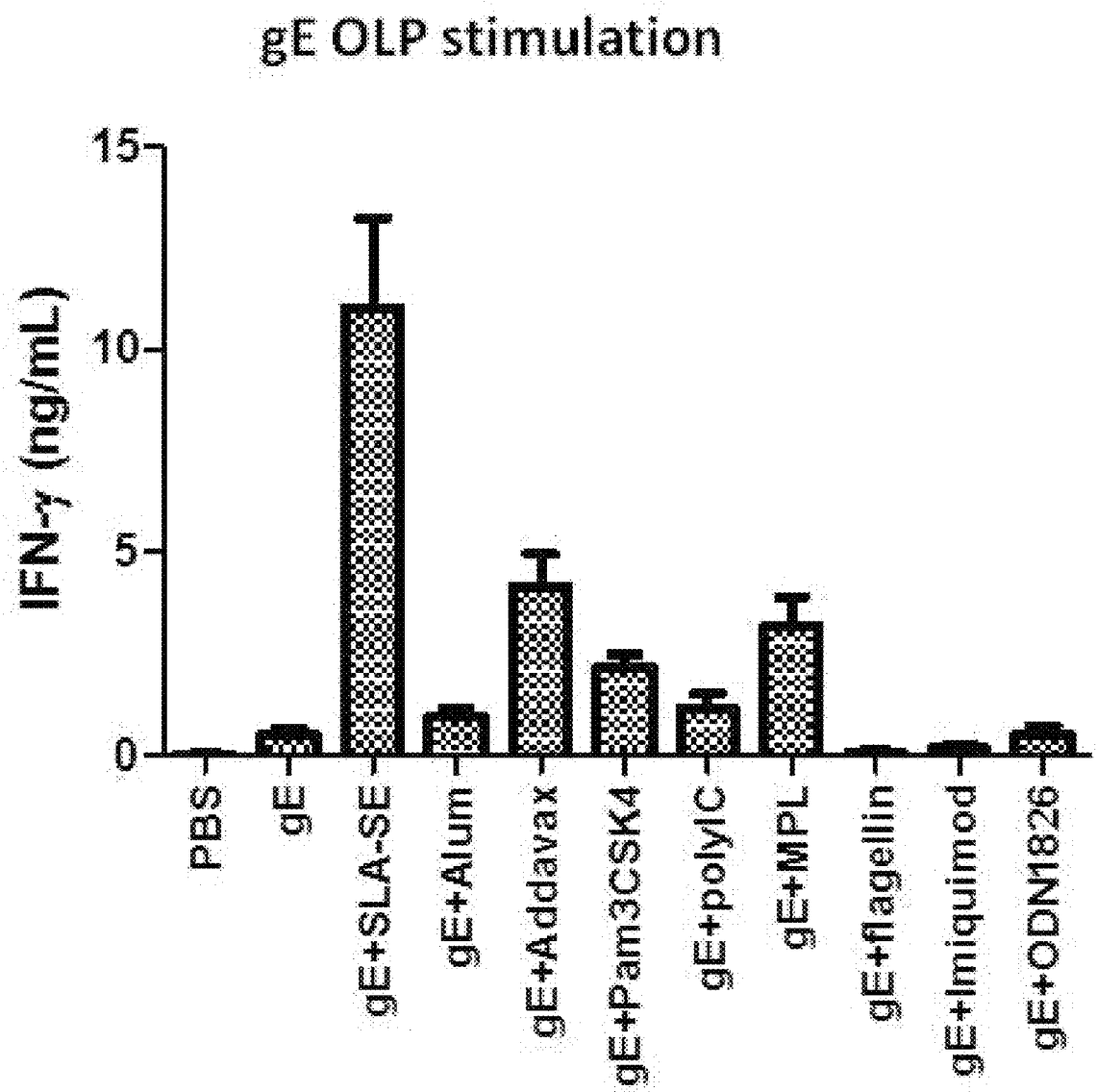

[Fig. 20]
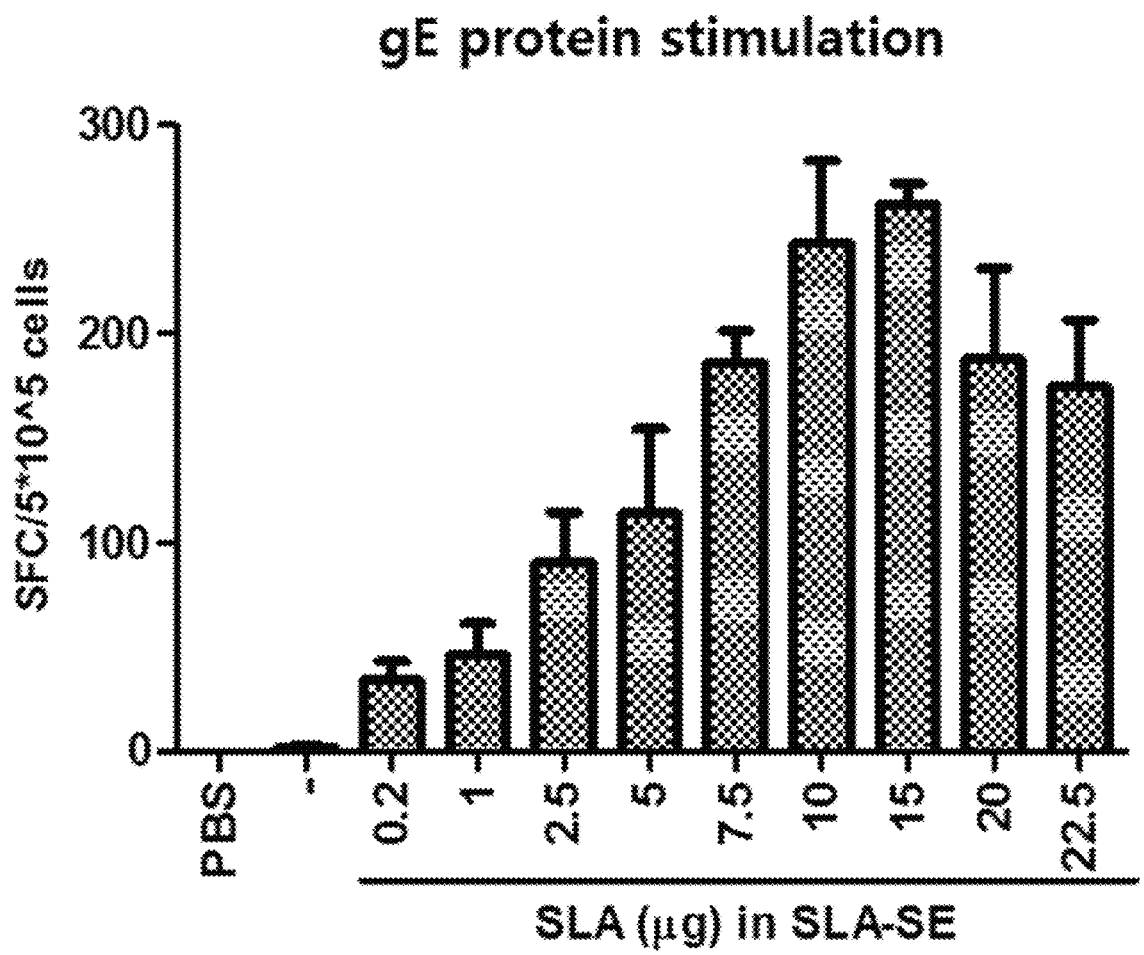

[Fig. 21]
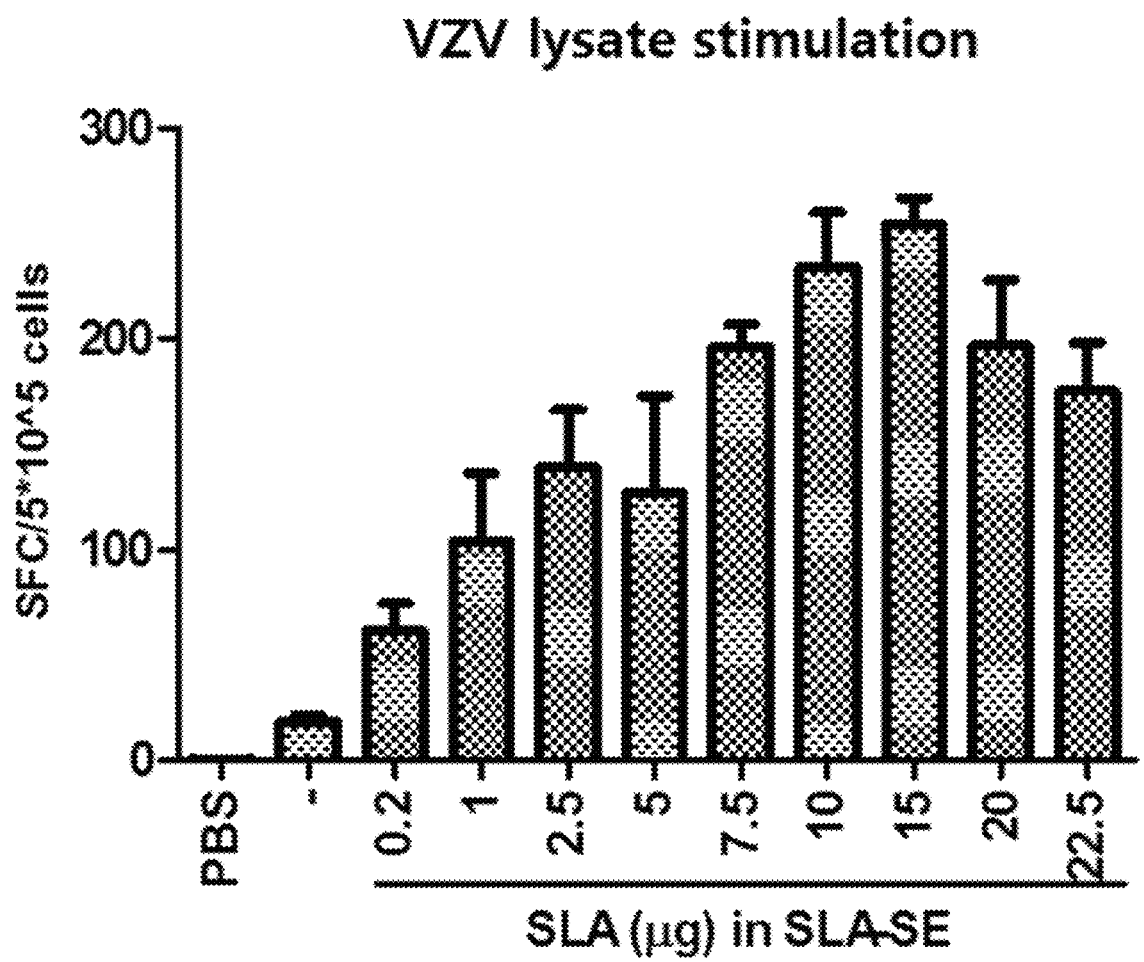

HERPES ZOSTER VACCINE COMPOSITION

CROSS REFERENCE TO RELATED APPLICATIONS

This application is a National Stage of International Application No. PCT/KR2017/015155 filed Dec. 20, 2017, claiming priority based on Korean Patent Application No. 10-2016-0178793 filed Dec. 26, 2016 & 10-2017-0176122 filed Dec. 20, 2017.

PARTIES TO A JOINT RESEARCH AGREEMENT

The presently claimed invention was made by or on behalf of the below listed parties to a joint research agreement. The joint research agreement was in effect on or before the date the claimed invention was made and prior to the effective filing date of the instant application, and the claimed invention was made as a result of activities undertaken within the scope of the joint research agreement. The parties to the joint research agreement are MOGAM INSTITUTE FOR BIOMEDICAL RESEARCH (formerly MOGAM BIOTECHNOLOGY INSTITUTE) and INFECTIOUS DISEASE RESEARCH INSTITUTE.

TECHNICAL FIELD

The present invention relates to a vaccine composition for preventing herpes zoster.

BACKGROUND ART

The primary infection of varicella-zoster virus (VZV) causes chickenpox which is characterized by highly contagious skin rashes mainly on the face and trunk. After the initial infection, the viral DNA can remain dormant for years in the cytoplasm of the host neuronal cell. The virus can be reactivated to cause herpes zoster (zoster or shingles) in adults.

Herpes zoster causes skin rashes distinct from those produced during the primary infection. The rashes are accompanied by severe pain and may lead to more severe conditions such as post-herpetic neuralgia (PHN).

Varicella-zoster virus (VZV), also known as human herpesvirus 3 (HHV-3), is a member of the alphaherpesvirus subfamily of the Herpesviridae family. VZV is an enveloped virus with a double-stranded DNA genome of about 125,000 nucleotides. The genome of VZV is enclosed by an icosahedral nucleocapsid. A viral tegument (epidermis), located in the space between the nucleocapsid and the viral envelope, is a construct consisting of virally-encoded proteins and enzymes. The viral envelope is derived from host cell membranes and contains virally-encoded glycoproteins.

The VZV genome encodes seventy (70) or more open reading frames (ORFs), nine (9) of which encode glycoproteins (gE, gI, gB, gH, gK, gN, gL, gC, and gM) that are presumed to function at different stages in the viral replication cycle.

Glycoprotein E (gE) is essential for viral replication (Mallory et al. (1997) *J. Virol.* 71: 8279-8288) and Mo et al. (2002) *Virology* 304: 176-186), and is the most abundant glycoprotein found in infected cells as well as in mature virions (Grose, 2002, The predominant varicella-zoster virus gE and gI glycoprotein complex, In Structure-function relationships of human pathogenic viruses, Holzenburg and Bogner (eds.), Kluwer Academic/Plenum Publishers, New York, N.Y.).

Glycoprotein I (gI) forms a complex with gE in infected cells, thereby promoting endocytosis of both glycoproteins, which are then delivered to the trans-Golgi where the final viral envelope is obtained (Olson and Grose (1998) *J. Virol.* 72: 1542-1551).

Glycoprotein B (gB), which is thought to play an important role in viral entry, has an epitope for a virus neutralizing antibody and is the second most glycoprotein on the virion surface (Arvin (1996) *Clin. Microbiol. Rev.* 9: 361-381).

Glycoprotein H (gH) is thought to have a fusion function that promotes cell-to-cell spread of the virus.

Currently, live attenuated vaccines, which are commonly used to prevent chickenpox or herpes zoster, have several disadvantages. First, there is some evidence that the immunity against VZV infection decreases with time and the effect of the vaccine disappears (Chaves et al. (2007) *N. Engl. J. Med.* 356: 1121-1129). Thus, the subjects vaccinated with the vaccine may remain susceptible to herpes zoster, which is a more severe condition caused by VZV. In addition, attenuated live vaccines are manufactured using live viruses with weakened pathogenicity, so that vaccination subjects may become susceptible to chickenpox or herpes zoster due to vaccination. In fact, there are several cases of herpes zoster reported to have been caused by the virus strain used in the vaccine (Matsubara et al. (1995) *Acta Paediatr Jpn* 37: 648-50; and Hammerschlag et al. (1989) *J Infect Dis.* 160: 535-7). In addition, due to the live attenuated virus present in the vaccine, the use of the vaccine may be limited for subjects whose immune function is decreased.

In order to increase the effect of preventing herpes zoster which re-emerges along the neuronal cells after the dormancy of the virus, it is important to significantly enhance the activation of cell-mediated immunity (CMI) to VZV antigen rather than the activation of humoral immunity thereto. For this, it is important to increase Th1/Th2 ratio by promoting the activation of Th1 among Th1 and Th2, which are T cells (helper T cells).

Therefore, there is a need to develop new herpes zoster vaccine compositions that can selectively increase the cell mediated immune response without having the disadvantages of live attenuated vaccines.

DISCLOSURE OF INVENTION

Technical Problem

The object of the present invention is to provide a vaccine composition having a high safety and an excellent effect of preventing herpes zoster, which selectively increases the cell mediated immune response without having the disadvantages of live attenuated vaccines.

Solution to Problem

1. A vaccine composition against chickenpox or herpes zoster comprising:

glycoprotein E of varicella-zoster virus;

a glucopyranosyl lipid adjuvant of the following Formula 1; and a metabolisable oil:

[Formula 1]

wherein, $R^1$, $R^3$, $R^5$ and $R^6$ are each independently $C_{10}$-$C_{12}$ alkyl; and $R^2$ and $R^4$ are each independently $C_8$-$C_{14}$ alkyl.

2. The vaccine composition of the above 1, wherein the glucopyranosyl lipid adjuvant is the one of Formula 1 wherein $R^1$, $R^3$, $R^5$ and $R^6$ are $C_{11}$ alkyl.

4. The vaccine composition of the above 1, wherein the glucopyranosyl lipid adjuvant is the one of Formula 1 wherein $R^2$ and $R^4$ are $C_9$ alkyl.

5. The vaccine composition of the above 1, wherein the metabolisable oil is squalene.

6. The vaccine composition of the above 5, wherein the squalene is contained in an amount of 1% (v/v) to 7% (v/v) of the total vaccine composition.

7. The vaccine composition of the above 6, wherein the squalene is contained in an amount of 1% (v/v) to 4% (v/v) of the total vaccine composition.

8. The vaccine composition of the above 1, wherein the glycoprotein E is contained in an amount of 5 μg to 100 μg in a single dose of the vaccine composition.

9. The vaccine composition of the above 1, wherein the glucopyranosyl lipid adjuvant is contained in an amount of 7.5 μg to 20 μg in a single dose of the vaccine composition.

10. The vaccine composition of the above 9, wherein the glucopyranosyl lipid adjuvant is contained in an amount of 9 μg to 18 μg in a single dose of the vaccine composition.

11. A method for preventing or treating chickenpox or herpes zoster comprising administering the composition of any one of the above 1 to 10 to a subject.

Advantageous Effects of Invention

The vaccine composition of the present invention is excellent in preventing herpes zoster.

The vaccine composition of the present invention significantly increases the cell mediated immune response to the VZV antigen as compared to the humoral immune response thereto.

The vaccine composition of the present invention greatly increases the number of Th1 cells producing two or more Th1-specific cytokines.

The vaccine composition of the present invention greatly increases the production of IgG2c as compared to the production of IgG1.

The vaccine composition of the present invention has no possibility of infecting subject with herpes zoster due to vaccination.

The vaccine composition of the present invention can be administered even to subjects whose immune function is decreased.

The vaccine composition of the present invention has a long-lasting preventive effect.

BRIEF DESCRIPTION OF DRAWINGS

FIG. 1 illustrates the production of gE antigen-specific IgG according to the experiment of Experimental Example 3.

FIG. 2 depicts the productions of gE antigen-specific IgG2c and IgG1 according to the experiment of Experimental Example 3.

FIG. 3 indicates the number of T cells that secrete IFN-γ specifically to gE protein according to the experiment of Experimental Example 4.

FIG. 4 demonstrates the number of T cells that secrete IFN-γ specifically to the gE overlapping peptide according to the experiment of Experimental Example 4.

FIG. 5 displays the number of T cells that secrete IFN-γ specifically to the entire VZV according to the experiment of Experimental Example 4.

FIG. 6 presents the amount of various Th cytokines secreted specifically to the gE antigen according to the experiment of Experimental Example 5.

FIG. 7 shows the distribution of gE antigen-specific cytokine-secreting cells according to the experiment of Experimental Example 6.

FIG. 8 illustrates the production of VZV antigen-specific IgG according to the experiment of Experimental Example 7.

FIG. 9 depicts the productions of VZV antigen-specific IgG2c and IgG1 according to the experiment of Experimental Example 7.

FIG. 10 indicates the amount of IFN-γ secreted specifically to the entire VZV according to the experiment of Experimental Example 8.

FIG. 11 demonstrates the distribution of VZV antigen-specific cytokine-secreting cells according to the experiment of Experimental Example 9.

FIG. 12 displays the production of VZV antigen-specific IgG according to the experiment of Experimental Example 10 and the number of T cells specific for gE or entire VZV according to the experiment of Experimental Example 2-2.

FIG. 13 presents the production of gE antigen-specific IgG according to the experiment of Experimental Example 11.

FIG. 14 shows the productions of gE antigen-specific IgG2c and IgG1 according to the experiment of Experimental Example 11.

FIG. 15 illustrates the number of T cells that secrete IFN-γ specifically to gE protein according to the experiment of Experimental Example 12.

FIG. 16 depicts the number of T cells that secrete IFN-γ specifically to the gE overlapping peptide according to the experiment of Experimental Example 12.

FIG. 17 indicates the number of T cells that secrete IFN-γ specifically to the VZV antigen according to the experiment of Experimental Example 12.

FIG. 18 demonstrates the amount of IFN-γ secreted by the gE protein stimulation according to the experiment of Experimental Example 13.

FIG. 19 displays the amount of IFN-γ secreted by the gE overlapping peptide stimulation according to the experiment of Experimental Example 13.

FIG. 20 presents the number of T cells that secrete IFN-γ specifically to gE protein according to the experiment of Experimental Example 14.

FIG. 21 shows the number of T cells that secrete IFN-γ specifically to the entire VZV according to the experiment of Experimental Example 14.

BEST MODE FOR CARRYING OUT THE INVENTION

The present invention relates to a herpes zoster vaccine composition, which comprises glycoprotein E of varicella-zoster virus, a glucopyranosyl lipid adjuvant, and a metabolisable oil, and has a high safety and an excellent effect of preventing herpes zoster by selectively increasing the cell mediated immune response without having the disadvantages of live attenuated vaccines.

Hereinafter, the present invention will be described in detail.

The vaccine composition of the present invention comprises glycoprotein E of varicella-zoster virus (VZV), a glucopyranosyl lipid adjuvant of the following Formula 1, and a metabolisable oil:

[Formula 1]

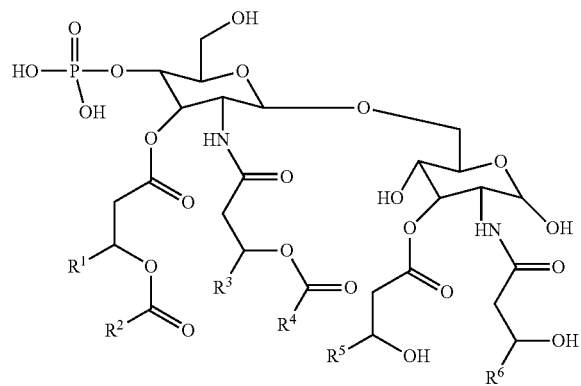

wherein, $R^1$, $R^3$, $R^5$ and $R^6$ are each independently $C_{10}$-$C_{12}$ alkyl; and $R^2$ and $R^4$ are each independently $C_8$-$C_{10}$ alkyl.

The vaccine composition of the present invention comprises glycoprotein E (gE) of VZV. Glycoprotein E (gE) in the present invention means glycoprotein E of VZV or an immunogenic derivative thereof. The immunogenic derivative in the present invention may be the one wherein a part of glycoprotein E is modified. For example, it may be the one wherein a part of glycoprotein E is cut, one or more amino acids of glycoprotein E are replaced by another amino acids, one or more amino acids of glycoprotein E are removed, one or more amino acids are added to glycoprotein E, or one or more amino acids of glycoprotein E are chemically modified. For example, glycoprotein E of the present invention may be represented by the sequence of SEQ ID NO: 1.

The vaccine composition of the present invention comprises a glucopyranosyl lipid adjuvant of the following Formula 1 and a metabolisable oil:

[Formula 1]

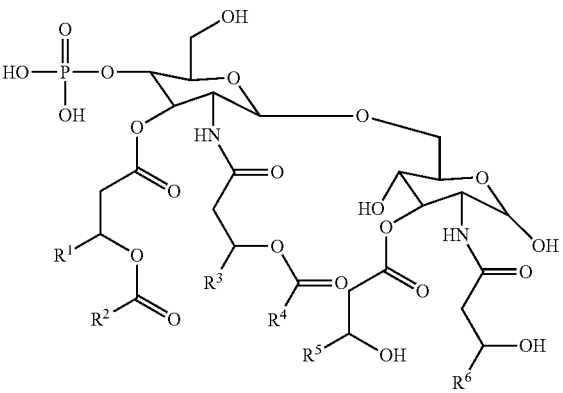

wherein, $R^1$, $R^3$, $R^5$ and $R^6$ are each independently $C_{10}$-$C_{12}$ alkyl; and $R^2$ and $R^4$ are each independently $C_8$-$C_{10}$ alkyl. For example, $R^2$ and $R^4$ may be $C_8$ alkyl, $C_9$ alkyl, or $C_{10}$ alkyl. According to a more specific example, $R^2$ and $R^4$ may be $C_9$ alkyl or $C_{10}$ alkyl. For example, $R^2$ and $R^4$ may be $C_9$ alkyl.

The term "metabolisable oil" as used herein means an oil whose structure is modified by metabolism, and includes vegetable oils, fish oils, animal oils, and synthetic oils, which have no biotoxicity and may undergo structural changes upon metabolic progression.

According to a specific embodiment of the present invention, the metabolisable oil of the present invention is squalene. Squalene is a hydrocarbon of triterpene backbone having 30 carbons. A variety of squalenes commonly known in the art to be used as metabolisable oils or emulsions may be used, for example, squalene from shark liver oil. An exemplary composition of squalene is described in Fox C B et al. (2013) *Vaccine* 31 (49): 5848-55.

In order to increase the effect of preventing herpes zoster, it is important to significantly enhance the activation of cell mediated immunity (CMI) to VZV antigens while minimizing the activation of humoral immunity thereto.

High levels of Th2-specific cytokines favor induction of a humoral immune response to the provided antigen, while high levels of Th1-specific cytokines tend to prefer induction of cell mediated immune response (CMI) to the provided antigen. Thus, the more Th1-specific cytokines are generated than the Th2-specific cytokine, the higher the degree of activation of the cell mediated immune response becomes than that of the humoral immune response.

Also, the greater the number of cells simultaneously producing two or more cytokines out of IFN-γ, TNF-α, and IL-2, the higher the degree of activation of the cell mediated immune response.

In addition, as the degree of activation of the cell mediated immune response becomes higher than that of the humoral immune response, the production of IgG2c antibody is greatly increased as compared to that of IgG1 antibody.

The vaccine composition of the present invention can greatly increase the degree of activation of the cell mediated immune response rather than that of the humoral immune response in the body of a subject.

For example, the vaccine composition of the present invention can significantly increase the production of Th1-specific cytokines (e.g., interferon-gamma (IFN-γ), tumor necrosis factor-alpha (TNF-α), and interleukin-2 (IL-2)) as compared to the production of Th2-specific cytokines (e.g., interleukin-4 (IL-4), interleukin-6 (IL-6), interleukin-10 (IL-10), and the like), in the body of a subject.

Also, for example, the vaccine composition of the present invention is capable of greatly increasing the number of cells simultaneously producing two or more cytokines out of IFN-γ, TNF-α, and IL-2 than the number of cells producing only one cytokine out of the above cytokines, among activated Th1 cells.

In addition, for example, the vaccine composition of the present invention can greatly increase the production of gE-specific IgG antibodies in the body of a subject and, especially, can greatly increase the production of gE-specific IgG2c antibodies as compared to that of gE-specific IgG1 antibodies.

The vaccine composition of the present invention may contain 5 µg to 100 µg of glycoprotein E in a single dose. For example, it may contain 5 µg to 80 µg, specifically 5 µg to 70 µg, more specifically 5 µg to 60 µg, and most specifically 5 µg to 50 µg of glycoprotein E in a single dose.

The vaccine composition of the present invention may contain 7.5 µg to 20 µg, specifically 9 µg to 18 µg, more specifically, 9 µg to 16 µg, and most specifically 10 µg to 15 µg of the glucopyranosyl lipid adjuvant in a single dose. According to another embodiment of the present invention, the vaccine composition of the present invention may contain 13 µg to 17 µg of the glucopyranosyl lipid adjuvant in a single dose. When the glucopyranosyl lipid adjuvant is included in the above range, the cell mediated immune response can be selectively maximized.

The vaccine composition of the present invention may contain 1 to 7% (v/v), more specifically 1 to 5% (v v), and most specifically 1 to 4% (v/v) of the metabolisable oil in a single dose.

In addition to glycoprotein E, the glucopyranosyl lipid adjuvant, and the metabolisable oil, the vaccine composition of the present invention may include pharmaceutically acceptable excipients, carriers, and the like. For example, the vaccine composition of the present invention may contain physiological saline or PBS (phosphate buffered saline).

The vaccine composition of the present invention can be formulated and packaged in various forms. According to one embodiment, the first vial containing glycoprotein E but not comprising the glucopyranosyl lipid adjuvant and the metabolisable oil, and the second vial containing the glucopyranosyl lipid adjuvant and the metabolisable oil but not comprising glycoprotein E may be separately packaged, and mixed prior to use (bedside mixing). According to another embodiment, a vaccine composition comprising all of glycoprotein E, the glucopyranosyl lipid adjuvant and the metabolic oil may be packaged in a vial, a syringe (prefilled syringe), or the like.

MODE FOR THE INVENTION

Hereinafter, the present invention will be described in more detail with reference to experimental examples. These experimental examples are only intended to illustrate the present invention, and the scope of the present invention is not limited to those exemplified in these experimental examples.

Experimental Example 1: Immunization

Since humans have a history of chickenpox infection, in order to mimic chickenpox infection in mice, live attenuated vaccine (LAV, 3000 pfu) was subcutaneously injected once to female C57BL/6 mice to perform primary immunization (LAV priming). After 28 days from the LAV priming (Day 0), various VZV vaccine compositions with or without VZV protein immunogen or adjuvant were administered by intramuscular injection to perform secondary immunization.

In order to measure the humoral immune response to VZV, blood samples were taken once at the LAV priming point, and 28 days and 42 days thereafter (Day 0, Day 28 and Day 42), respectively, and leukocytes were collected from spleen samples 42 days after the LAV priming (Day 42) to measure CMI (cell-mediated immune response) against VZV.

The experimental design for primary immunization (LAV priming), secondary immunization (Immunization), and immune response measurement is summarized as shown in Table 1 below. In Table 1 below, gE refers to VZV glycoprotein E of SEQ ID NO: 1, LAV refers to live attenuated virus, SLA refers to the glucopyranosyl lipid adjuvant of Formula 1 wherein $R^2$ and $R^4$ are $C_9$ alkyl, and SE refers to squalene. SLA and squalene were obtained from the Infectious Disease Research Institute (Seattle, US) and Sigma-Aldrich (St. Louis, Mo.), respectively.

Alum hydroxide is aluminum hydroxide; Addavax® is a squalene-based oil-in-water nano-emulsion; Pam3CSK4 is a TLR 1/2 agonist, a synthetic triacylated lipoprotein of CAS number 112208-00-1; polyIC is polyinosinic-polycytidylic acid; MPL is Monophosphoryl Lipid A; and ODN1826 is a Class B CpG oligonucleotide-Murine TLR9 ligand. In addition, the days of immunization, blood sample collection, and spleen sample collection were calculated from Day 0 as the day of LAV priming.

TABLE 1

| Group | Primary immunization (LAV priming*) | Secondary immunization (Immunization) | | Day of secondary immunization | Day of blood sample collection | Day of spleen sample collection |
|---|---|---|---|---|---|---|
| | | Antigen | Adjuvant | | | |
| PBS | PBS-only | X | X | Day 28 | Day 0, Day 28, Day 42 | Day 42 |
| LAV(1 shot) | LAV | PBS-only | X | | | |
| LAV(2 shot) | LAV | LAV (15,000 pfu) | X | | | |
| gE | LAV | gE (5 µg) | X | | | |
| gE + SLA-AF | LAV | gE (5 µg) | SLA (5 µg) in aqueous formulation | | | |
| gE + SLA-SE | LAV | gE (5 µg) | SLA (5 µg) + SE (2%) | | | |
| gE + SE | LAV | gE (5 µg) | SE (2%) | | | |
| gE + liposome | LAV | gE (5 µg) | liposome-only | | | |
| gE + Addavax | LAV | gE (5 µg) | Addavax (50%) | | | |

TABLE 1-continued

| Group | Primary immunization (LAV priming*) | Secondary immunization (Immunization) | | Day of secondary immunization | Day of blood sample collection | Day of spleen sample collection |
|---|---|---|---|---|---|---|
| | | Antigen | Adjuvant | | | |
| gE + MPL + QuilA | LAV | gE (5 µg) | MPL (5 µg) + QuilA (5 µg) | | | |
| gI + SLA-SE | LAV | gI (5 µg) | SLA (5 µg) + SE (2%) | | | |
| IE63 + SLA-SE | LAV | IE63 (5 µg) | SLA (5 µg) + SE (2%) | | | |
| gB + SLA-SE | LAV | gB (5 µg) | SLA (5 µg) + SE (2%) | | | |
| gC + SLA-SE | LAV | gC (5 µg) | SLA (5 µg) + SE (2%) | | | |
| gL + SLA-SE | LAV | gL (5 µg) | SLA (5 µg) + SE (2%) | | | |
| gE + Alum hydroxide | LAV | gE (5 µg) | Alum hydroxide (0.5 mg) | | | |
| gE + Addavax | LAV | gE (5 µg) | Addavax (50 µL) | | | |
| gE + Pam3CSK4 | LAV | gE (5 µg) | Pam3CSK4 (11 µg) | | | |
| gE + polyIC | LAV | gE (5 µg) | polyIC (55 µg) | | | |
| gE + MPL | LAV | gE (5 µg) | MPL (11 µg) | | | |
| gE + flagellin | LAV | gE (5 µg) | Flagellin (5.5 µg) | | | |
| gE + imiquimod | LAV | gE (5 µg) | Imiquimod (55 µg) | | | |
| gE + ODN1826 | LAV | gE (5 µg) | ODN1826 (35 µg) | | | |

*Primary immunization (LAV priming): Dose 100 µL/head. 3,000 pfu
*Secondary immunization (Immunization): Dose 100 µL/head Experimental Example 2: Experimental Methods Experimental Example 2-1: Method for Measuring VZV Antigen-Specific IgG Titer (VZV Specific IgG Titer)

After performing the primary immunization and the secondary immunization, ELISA (enzyme-linked immunosorbant assay) was carried out for measuring VZV antigen-specific IgG titer. A recombinant gE protein or VZV antigen (1 µg/mL) was coated onto an ELISA plate and incubated overnight at 4° C. The ELISA plate was washed three times and blocking was carried out with PBS (Phosphate-buffered saline) solution containing 2% BSA (Bovine serum albumin) for 1 hour. After washing the ELISA plate, diluted serum samples were added thereto and incubated for 2 hours. HRP (Horseradish peroxidase)-conjugated goat anti-mouse IgG, IgG1, or IgG2c antibodies were added thereto and incubated for 1 hour. After the final incubation, the ELISA plate was washed and the HRP reaction was induced by the addition of TMB (3, 3', 5, 5'-tetramethylbenzidine) substrate. The HRP reaction was stopped by adding ELISA stop solution and optical density (OD) was measured using a spectrometer at a wavelength of 450 nm.

Experimental Example 2-2: Method for Measuring VZV Antigen-Specific Cell-Mediated Immune Response Using the Enzyme-Linked Immunospot Assay (ELISPOT Assay)

After performing the primary immunization and the secondary immunization, mouse IFN-γ ELISPOT (enzyme-linked immunospot) assay was carried out to confirm VZV antigen-specific cell-mediated immune response (CMI). IFN-γ capture antibody (5 µg/mL) was coated onto an ELISPOT plate and incubated overnight at 4° C. The ELISPOT plate was washed 3 times and blocking was carried out with a medium containing 10% FBS (fetal bovine serum) for 1 hour. After washing the ELISPOT plate, leukocytes collected from the immunized mice and gE protein, gE OLP (overlapping peptide), or a VZV lysate were added thereto and incubated for 24 hours for leukocyte stimulation. Upon completion of the leukocyte stimulation, the ELISPOT plate was washed, and biotinylated mouse IFN-γ detection antibody (2 µg/mL) was added thereto and incubated. After washing the plate, streptavidin-HRP was added thereto and incubated again. Then, after washing the ELISPOT plate, AEC substrate mixture was added thereto to induce a reaction at room temperature. The reaction was stopped by washing the ELISPOT plate with water and the plate was dried. The number of the resulting spots were counted with a device.

Experimental Example 2-3: Method for Identifying Cytokines Secreted by Antigen Stimulation (CBA Assay)

After performing the primary immunization and the secondary immunization, CBA (cytometric bead array) assay was carried out to identify the types of cytokines secreted by T cells due to antigen stimulation. Leukocytes collected from mice were stimulated with gE protein or a VZV lysate for 3 days and centrifuged to obtain the supernatant, which was then assayed for cytokines with mouse Th1/Th2/Th17 CBA kit. Seven (7) kinds of cytokine capture beads (IL-2, IL-4, IL-6, IL-10, IFN-γ, TNF, and IL-17A), the supernatant sample, and cytokine detection beads were reacted together for 2 hours, the beads were washed, and the amounts of cytokines in the supernatant were determined.

Experimental Example 2-4: Method for Determining the Distribution of Cytokine-Secreting Cells (ICS Assay)

After performing the primary immunization and the secondary immunization, the secretion of Th1-specific cytokines was measured by ICS (intracellular cytokine staining) assay to confirm the antigen-specific cell-mediated immune response. Leukocytes collected from mice were stimulated overnight with gE protein and, at this time, GolgiStop (BFA)/GolgiPlug (monensin) was also added to prevent cytokines in the cells from being secreted to the outside. After washing the stimulated leukocytes, the cell surface of leukocytes was labeled with antibodies (7-AAD, CD3-FITC, CD4-V500) to identify T cells. After the completion of the reaction, the leukocytes were washed, permeabilized, and subjected to a reaction with antibodies (TNF-α-PE, IFN-γ-APC, IL-2-V450) which can be bound to cytokines to confirm the presence of cytokines in the cells. After the reaction, the leukocytes were washed and fixed, and the distribution of the cells secreting cytokines by the antigen stimulation was analyzed.

Experimental Example 2-5: Method for Determining IFN-γ Cytokine Secreted by gE Antigen Stimulation (IFN-γ ELISA)

After performing the primary immunization and the secondary immunization, IFN-γ ELISA assay was carried out to determine the secretion amount of IFN-γ, a typical effector cytokine secreted by T cells by antigen stimulation. Leukocytes collected from mice were stimulated with gE protein or gE overlapping peptide for 3 days and centrifuged to obtain the supernatant, which was then analyzed with a mouse IFN-γ ELISA kit. IFN-γ capture antibody (4 μg/mL) was coated onto an ELISA plate and incubated overnight at room temperature. The ELISA plate was washed three times and blocking was carried out with PBS containing 1% bovine serum albumin (BSA) for 1 hour. After washing the ELISA plate, the supernatant obtained by stimulating leukocytes was added thereto and incubated at room temperature for 2 hours. After washing the ELISA plate, biotinylated mouse IFN-γ detection antibody (400 ng/mL) was added thereto and incubated at room temperature for 2 hours. After washing, streptavidin-HRP was added thereto and incubated again for 20 minutes. After the incubation, the ELISA plate was washed and reacted with a substrate solution at room temperature for 20 minutes. After stopping the reaction with a stop solution, the optical density was measured using an instrument at 450 nm.

Experimental Example 3: Measurement of gE Antigen-Specific IgG Titer (gE Specific IgG Titer)

The gE antigen-specific IgG titer was measured according to the method of Experimental Example 2-1, and the results of the experiment are summarized in FIGS. 1 and 2.

As shown in FIG. 1, the production of gE antigen-specific IgG was greatly increased in the gE+SLA-SE group.

As shown in FIG. 2, the production of IgG2c was greatly increased in the gE+SLA-SE group and, especially, the production of IgG2c was greatly increased as compared to that of IgG1. In FIG. 2, the bar graphs on the right side based on the horizontal axis "0" represent the production of IgG2c, and the bar graphs on the left side represent the production of IgG1.

Taking the results of FIGS. 1 and 2 into consideration, it was confirmed that the use of a composition comprising gE, SLA, and SE significantly increased the overall IgG production and the production of IgG2c and, especially, greatly increased the production of IgG2c as compared to IgG1. These results means that the composition comprising gE, SLA, and SE, which satisfy both high IgG2c production and high IgG2c/IgG1 ratio, has the greatest effect of preventing herpes zoster.

Experimental Example 4: Measurement of gE or VZV Antigen-Specific Cell Mediated Immune Responses (ELISPOT Assay)

The gE protein, gE OLP, or VZV lysate-specific cell-mediated immune responses were measured according to the method of Experimental Example 2-2 (IFN-γ ELISPOT assay), and the experimental results are summarized in FIGS. 3, 4, and 5.

As shown in FIG. 3, when the number of T cells that specifically reacted with the gE protein after the secondary immunization was confirmed by ELISPOT assay, it can be seen that the number of T cells that secrete IFN-γ, a representative Th1 cytokine, increased when the combination of gE, SLA, and SE (gE+SLA-SE) was used.

As shown in FIG. 4, when the number of T cells specific for the gE overlapping peptide after the secondary immunization was confirmed by ELISPOT assay, it can be seen that, similar to the results of FIG. 3, the composition comprising gE, SLA, and SE showed significantly increased antigen-specific CMI as compared to other compositions.

As shown in FIG. 5, when the number of T cells specific for the entire VZV induced by stimulation with VZV lysate after immunization with the gE antigen was confirmed by ELISPOT assay, it was confirmed that the number of T cells that secrete effector cytokines specific for the entire VZV as well as the gE antigen was increased by the combination of gE, SLA, and SE.

Taking the results of FIGS. 3, 4, and 5 into consideration, it was confirmed that the composition comprising gE, SLA, and SE (gE+SLA-SE) can maximally increase VZV antigen-specific CMI as well as gE-specific CMI. This means that the gE+SLA-SE composition has a greater effect of preventing herpes zoster than other compositions.

Experimental Example 5: Confirmation of the Amount of Cytokines Secreted by Antigen Stimulation (CBA Assay)

The confirmation of the cytokines secreted by the antigen stimulation (CBA assay) was performed according to the method of Experimental Example 2-3, and the experimental results are summarized in FIG. 6. In FIG. 6, IFN-g means IFN-γ.

As shown in FIG. 6, various Th cytokines were secreted by the composition comprising gE, SLA, and SE, and a representative Th1 cytokine, IFN-γ (the fourth from the front), was greatly increased, whereas the secretion of Th2 cytokines, IL-4 (the second from the front) and IL-6 (the third from the front), or the Th17 cytokine, IL-17A (the sixth from the front), was minimal. This means that the composition comprising gE, SLA, and SE has a greater effect of preventing herpes zoster than other compositions.

Experimental Example 6: Confirmation of the Distribution of Cytokine-Secreting Cells The assay for confirming the distribution of the cells secreting cytokines by antigen stimulation (ICS assay) was performed according to the method of Experimental Example 2-4, and the results of the experiment are summarized in FIG. 7.

As shown in FIG. 7, in the case of the gE+SLA-SE group, the number of T cells that simultaneously secreted two or more Th1-specific cytokines significantly increased (69%), indicating that high quality antigen-specific T cells were induced by the immunization with gE+SLA-SE. This means that the composition comprising gE, SLA, and SE has a greater effect of preventing herpes zoster than other compositions.

Experimental Example 7: Measurement of VZV Antigen-Specific IgG Titers (Anti-VZV Glycoprotein Specific IgG Titer)

Various VZV antigen-specific IgG titers depending on the use of SLA-SE were determined in the same manner as in Experimental Example 2-1 except that any one of gE, gI, IE63, gB, gC, and gL was used as an antigen in the secondary immunization and SLA-SE was used as an adjuvant, and the results are summarized in FIGS. 8 and 9.

As shown in FIG. 8, the production of VZV antigen-specific IgG was significantly increased in the gE+SLA-SE group.

As shown in FIG. 9, the production of IgG2c was greatly increased in the gE+SLA-SE group and, especially, the production of IgG2c was significantly increased as compared to that of IgG1. In FIG. 9, the bar graphs on the right side based on the horizontal axis "0" represent the production of IgG2c, and the bar graphs on the left side represent the production of IgG1.

Taking the results of FIGS. 8 and 9 into consideration, it was confirmed that the use of the composition comprising gE, SLA, and SE significantly increased the overall IgG production and the production of IgG2c, and, especially, greatly increased the production of IgG2c as compared to IgG1. This means that the composition comprising gE, SLA, and SE, which satisfy both high IgG2c production and high IgG2c/IgG1 ratio, has the greatest effect of preventing herpes zoster.

Experimental Example 8: Confirmation of the Amount of Cytokines Secreted by VZV Antigen Stimulation An experiment (CBA assay) for confirming the cytokines secreted by antigen stimulation, following the immunization, was performed in the same manner as in Experimental Example 2-3 except that any one of gE, gI, IE63, gB, gC, and gL was used as an antigen in the secondary immunization and SLA-SE was used as an adjuvant, and the results are summarized in FIG. 10.

As shown in FIG. 10, in the case of the gE+SLA-SE group, the secretion amount of IFN-γ, a representative Th1 cytokine, was greatly increased. This means that cell-mediated immune response (CMI) was greatly activated, and that the composition comprising gE, SLA, and SE has a greater effect of preventing herpes zoster than other compositions.

Experimental Example 9: Confirmation of the Distribution of Cells Secreting VZV Antigen-Specific Cytokines An experiment (ICS assay) for confirming the distribution of T cells that secrete effector cytokines by antigen stimulation, following the immunization, was performed in the same manner as in Experimental Example 2-4 except that any one of gE, gI, IE63, gB, gC, and gL was used as an antigen in the secondary immunization and SLA-SE was used as an adjuvant, and the results are summarized in FIG. 11.

As shown in FIG. 11, in the case of the gE+SLA-SE group, the proportion of CD4$^+$ T cells that secrete Th1 cytokines IFN-γ, IL-2, and TNF-α was significantly increased. This means that cell-mediated immune response (CMI) was greatly activated, and that the composition comprising gE, SLA, and SE has a greater effect of preventing herpes zoster than other compositions.

Experimental Example 10: Identification of VZV-Specific Immunogenicity Depending on the Combination of Antigens In order to identify the VZV-specific immunogenicities induced when using the gE antigen alone and when using gE antigen in combination with another VZV antigen at the time of the secondary immunization, VZV antigen-specific IgG titers and VZV antigen-specific T cell immune responses were confirmed according to the methods of Experimental Examples 2-1 and 2-2, and the experimental results are summarized in FIG. 12.

As shown in FIG. 12, the VZV-specific antibody response and T cell response induced when the gE antigen was used alone were not significantly different from the VZV-specific immune responses induced when gE antigen was used together with gI or IE63 antigen. This means that a composition comprising gE, SLA, and SE has a greater effect of preventing herpes zoster than other compositions.

Experimental Example 11: Measurement of gE Antigen-Specific IgG Titers (gE Specific IgG Titer)

The gE antigen-specific IgG titers depending on the use of various adjuvant were measured in the same manner as in Experimental Example 2-1 except that gE was used as an antigen and any one of SLA-SE, alum hydroxide, Addavax, Pam3CSK4, polyIC, MPL, flagellin, Imiquimod, and ODN1826 was used as an adjuvant in the secondary immunization, and the results are summarized in FIGS. 13 and 14.

As shown in FIG. 13, the production of gE antigen-specific IgG was greatly increased in the gE+SLA-SE group, compared to other adjuvants groups.

As shown in FIG. 14, the production of IgG2c was greatly increased in the gE+SLA-SE group as compared to other adjuvants groups and, especially, the production of IgG2c was significantly increased as compared to that of IgG1. In FIG. 14, the bar graphs on the right side based on the horizontal axis "0" represent the production of IgG2c, and the bar graphs on the left side represent the production of IgG1.

Taking the results of FIGS. 13 and 14 into consideration, it was confirmed that the use of the composition comprising gE, SLA, and SE significantly increased the overall IgG production and the production of IgG2c. This means that the composition comprising gE, SLA, and SE has the greatest effect of preventing herpes zoster.

Experimental Example 12: Measurement of gE or VZV Antigen-Specific Cell Mediated Immune Responses (ELISPOT Assay)

The gE protein, gE OLP, or VZV lysate-specific cell-mediated immune responses were measured according to the method of Experimental Example 2-2 (IFN-γ ELISPOT assay), and the experimental results are summarized in FIGS. 15, 16, and 17.

As shown in FIG. 15, when the number of T cells specifically responding to the gE protein after the secondary immunization was confirmed by ELISPOT assay, it can be seen that the number of T cells that secrete IFN-γ, a representative Th1 cytokine, significantly increased in the gE+SLA-SE group as compared to other adjuvants groups.

As shown in FIG. 16, when the number of T cells specific for the gE overlapping peptide after the secondary immunization was confirmed by ELISPOT assay, it can be seen that, similar to the results of FIG. 15, the composition comprising gE, SLA, and SE showed significantly increased antigen-specific CMI as compared to other compositions.

As shown in FIG. 17, when the number of T cells specific for the entire VZV induced by stimulation with a VZV lysate after immunization with gE antigen was confirmed by ELISPOT assay, it was confirmed that the number of T cells that secrete IFN-γ specific for the entire VZV was increased by gE+SLA-SE.

Taking the results of FIGS. 15, 16, and 17 into consideration, it was confirmed that the composition comprising gE, SLA, and SE can maximally increase VZV antigen-specific CMI as well as gE-specific CMI, compared to other compositions. This means that the gE+SLA-SE composition has a greater effect of preventing herpes zoster than other compositions.

Experimental Example 13: Confirmation of IFN-γ Cytokine Secreted by gE Antigen or VZV Antigen Stimulation (IFN-γ ELISA Assay)

An experiment (IFN-γ ELISA assay) for confirming IFN-γ cytokine secreted by gE antigen or gE OLP antigen stimulation was performed according to the method of Experimental Example 2-5, and the results are summarized in FIGS. 18 and 19.

As shown in FIG. 18, when the secretion amount of IFN-γ cytokine secreted by gE protein stimulation after the secondary immunization was observed, it was confirmed that the secretion amount of IFN-γ, a typical Th1 effector cytokine, in the gE+SLA-SE group was increased as compared to other adjuvant groups.

As shown in FIG. 19, when the secretion amount of IFN-γ cytokine secreted by gE overlapping peptide stimulation after the secondary immunization was observed, it was confirmed that the secretion amount of IFN-γ was increased by the combination of gE, SLA, and SE as compared to other adjuvant groups.

Taking the results of FIGS. 18 and 19 into consideration, the composition comprising gE, SLA, and SE increased the secretion amount of a representative Th1 effector cytokine, compared to other adjuvant-containing compositions, and this means that the gE+SLA-SE composition has a greater effect of preventing herpes zoster than other compositions.

Experimental Example 14: Determination of the Optimum Amount of SLA-SE Inducing VZV-Specific Immunogenicity Table 2 summarizes the experimental design for confirming the optimum amount of SLA-SE that can most effectively induce VZV antigen-specific cell-mediated immune response (CMI). Live attenuated vaccine (LAV, 3,000 pfu) was subcutaneously injected once to female C57BL/6 mice and, on day 28 thereafter, the secondary immunization (immunization) was performed. On day 56 after the LAV priming, leukocytes were collected from spleen samples to confirm cell-mediated immune response (CMI) specific for VZV.

TABLE 2

| Group | Primary immunization (LAV priming*) | Secondary immunization (Immunization) | | Day of secondary immunization | Day of spleen sample collection |
|---|---|---|---|---|---|
| | | Antigen | Adjuvant | | |
| PBS | PBS-only | X | X | Day 28 | Day 56 |
| gE | LAV | gE (5 μg) | X | | |
| gE + SLA 0.2 μg | LAV | gE (5 μg) | SLA (0.2 μg) + SE (2%) | | |
| gE + SLA 1 μg | LAV | gE (5 μg) | SLA (1 μg) + SE (2%) | | |
| gE + SLA 2.5 μg | LAV | gE (5 μg) | SLA (2.5 μg) + SE (2%) | | |
| gE + SLA 5 μg | LAV | gE (5 μg) | SLA (5 μg) + SE (2%) | | |
| gE + SLA 7.5 μg | LAV | gE (5 μg) | SLA (7.5 μg) + SE (2%) | | |
| gE + SLA 10 μg | LAV | gE (5 μg) | SLA (10 μg) + SE (2%) | | |
| gE + SLA 15 μg | LAV | gE (5 μg) | SLA (15 μg) + SE (2%) | | |
| gE + SLA 20 μg | LAV | gE (5 μg) | SLA (20 μg) + SE (2%) | | |
| gE + SLA 22.5 μg | LAV | gE (5 μg) | SLA (22.5 μg) + SE (2%) | | |

*Primary immunization (LAV priming): Dose 100 μL/head. 3,000 pfu
*Secondary immunization (Immunization): Dose 100 μL/head The gE antigen-specific cell-mediated immune response (IFN-γ ELISPOT assay) was measured according to the method of Experimental Example 2-2, and the results of the experiment are summarized in FIG. 20.

The VZV antigen-specific cell-mediated immune response (IFN-γ ELISPOT assay) was measured according to the method of Experimental Example 2-2, and the results of the experiment are summarized in FIG. 21.

Taking the results of FIGS. 20 and 21 into consideration, it can be seen that the optimum amount of SLA for inducing VZV antigen-specific cell-mediated immune response is in the range of 7.5 μg to 20 μg.

The invention claimed is:

1. A vaccine composition against chickenpox or herpes zoster comprising:
   glycoprotein E of varicella-zoster virus;
   a glucopyranosyl lipid adjuvant of the following Formula 1; and
   a squalene:

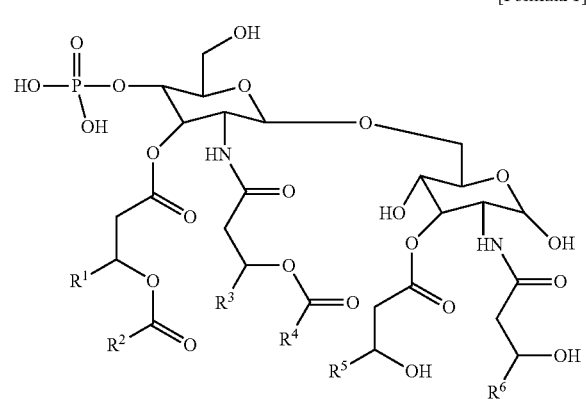

[Formula 1]

wherein,
R$^1$, R$^3$, R$^5$ and R$^6$ are each independently C$_{10}$-C$_{12}$ alkyl; and R$^2$ and R$^4$ are each independently C$_8$-C$_{10}$ alkyl.

2. The vaccine composition of claim 1, wherein the glucopyranosyl lipid adjuvant is the one of Formula 1 wherein R$^1$, R$^3$, R$^5$ and R$^6$ are C$_{11}$ alkyl.

3. The vaccine composition of claim 1, wherein the glucopyranosyl lipid adjuvant is the one of Formula 1 wherein R$^2$ and R$^4$ are C$_9$.

4. The vaccine composition of claim 1, wherein the glucopyranosyl lipid adjuvant is contained in an amount of 7.5 μg to 20 μg in a single dose of the vaccine composition.

5. The vaccine composition of claim 4, wherein the glucopyranosyl lipid adjuvant is contained in an amount of 9 μg to 18 μg in a single dose of the vaccine composition.

6. The vaccine composition of claim 1, wherein the squalene is contained in an amount of 1% (v/v) to 7% (v/v) of the total vaccine composition.

7. The vaccine composition of claim 6, wherein the squalene is contained in an amount of 1% (v/v) to 4% (v/v) of the total vaccine composition.

8. The vaccine composition of claim 1, wherein the glycoprotein E is contained in an amount of 5μg to 100 μg in a single dose of the vaccine composition.

* * * * *

SEQUENCE LISTING

<160> NUMBER OF SEQ ID NOS: 1

<210> SEQ ID NO 1
<211> LENGTH: 537
<212> TYPE: PRT
<213> ORGANISM: Human herpesvirus 3

<400> SEQUENCE: 1

```
Met Gly Thr Val Asn Lys Pro Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
            35                  40                  45

Ser Val Tyr Glu Pro Tyr Tyr His Ser Asp His Ala Glu Ser Ser Trp
        50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
        130                 135                 140

Lys Ile Val Asn Val Asp Gln Arg Gln Tyr Gly Asp Val Phe Lys Gly
145                 150                 155                 160

Asp Leu Asn Pro Lys Pro Gly Gln Arg Leu Ile Glu Val Ser Val
            165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
            245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
            290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
            355                 360                 365
```

```
Glu Ala Pro Phe Asp Leu Leu Leu Glu Trp Leu Tyr Val Pro Ile Asp
    370             375             380
Pro Thr Cys Gln Pro Met Arg Leu Tyr Ser Thr Cys Leu Tyr His Pro
385             390             395             400
Asn Ala Pro Gln Cys Leu Ser His Met Asn Ser Gly Cys Thr Phe Thr
            405             410             415
Ser Pro His Leu Ala Gln Arg Val Ala Ser Thr Val Tyr Gln Asn Cys
            420             425             430
Glu His Ala Asp Asn Tyr Thr Ala Tyr Cys Leu Gly Ile Ser His Met
        435             440             445
Glu Pro Ser Phe Gly Leu Ile Leu His Asp Gly Gly Thr Thr Leu Lys
    450             455             460
Phe Val Asp Thr Pro Glu Ser Leu Ser Gly Leu Tyr Val Phe Val Val
465             470             475             480
Tyr Phe Asn Gly His Val Glu Ala Val Ala Tyr Thr Val Val Ser Thr
            485             490             495
Val Asp His Phe Val Asn Ala Ile Glu Glu Arg Gly Phe Pro Pro Thr
        500             505             510
Ala Gly Gln Pro Pro Ala Thr Thr Lys Pro Lys Glu Ile Thr Pro Val
    515             520             525
Asn Pro Gly Thr Ser Pro Leu Leu Arg
530             535
```